US00RE40471E

(19) United States
(12) Reissued Patent
Groenke et al.

(10) Patent Number: US RE40,471 E
(45) Date of Reissued Patent: Aug. 26, 2008

(54) AED WITH FORCE SENSOR

(75) Inventors: Allen W. Groenke, Bloomington, MN (US); James E. Brewer, Cottage Grove, MN (US)

(73) Assignee: Cardiac Science, Inc., Bothell, WA (US)

(21) Appl. No.: 10/255,988

(22) Filed: Sep. 25, 2002

Related U.S. Patent Documents

Reissue of:
(64) Patent No.: 6,125,299
Issued: Sep. 26, 2000
Appl. No.: 09/182,831
Filed: Oct. 29, 1998

(51) Int. Cl.
*A61N 1/39* (2006.01)
*A61H 31/00* (2006.01)

(52) U.S. Cl. ..... 607/6; 607/3; 607/5; 600/16
(58) Field of Classification Search ..... 607/5–6, 607/3
See application file for complete search history.

(56) References Cited

U.S. PATENT DOCUMENTS

| | | | |
|---|---|---|---|
| 3,685,645 | A | 8/1972 | Kawaguchi |
| 3,857,398 | A | 12/1974 | Rubin |
| 3,862,636 | A | 1/1975 | Bell et al. |
| 4,034,854 | A | 7/1977 | Bevilacqua |
| 4,096,856 | A | 6/1978 | Smith et al. |
| 4,273,114 | A | 6/1981 | Barkalow et al. |
| 4,439,810 | A | 3/1984 | Shimada et al. |
| 4,610,254 | A | 9/1986 | Morgan et al. |
| 4,619,265 | A | 10/1986 | Morgan et al. |
| 4,776,350 | A | 10/1988 | Grossman et al. |
| 4,779,630 | A | 10/1988 | Scharnberg et al. |
| 4,919,144 | A | 4/1990 | Vandehey |
| 4,945,477 | A | 7/1990 | Edwards |
| 4,979,517 | A | 12/1990 | Grossman et al. |
| 5,150,708 | A | 9/1992 | Brooks |
| 5,228,449 | A | 7/1993 | Christ et al. |
| 5,237,989 | A | 8/1993 | Morgan et al. |

(Continued)

FOREIGN PATENT DOCUMENTS

| | | | |
|---|---|---|---|
| EP | 1 157 717 A1 | * | 11/2001 |
| WO | WO 99/24114 | * | 5/1999 |

*Primary Examiner*—Carl Layno
(74) *Attorney, Agent, or Firm*—Patterson, Thuente, Skaar & Christensen, PA

(57) ABSTRACT

A force sensor, for use in combination with an automated electronic defibrillator (AED), includes a first conductive layer. A second conductive layer is spaced apart from the first conductive layer such that no electrical communication occurs between the first and second conductive layers. An electrical communication device is provided for establishing electrical communication between the first and second conductive layers responsive to the application of a force to said electrical communication means. A method of prompting a rescuer in the application of cardiopulmonary resuscitation to a victim includes the steps of:

sensing a force applied by the rescuer to the victim's sternum;

sensing an interval between successive applications of force to the victim's sternum;

comparing the force applied by the rescuer to the victim's sternum to a standard of force known to effect resuscitation;

providing a prompt to the rescuer that prompts the rescuer to vary the force delivered to approximate the force that is known to effect resuscitation, comparing the interval between successive applications of force to the victim's sternum to a standard interval known to effect resuscitation; and providing a prompt to the rescuer that prompts the rescuer to vary the interval of force application to approximate the interval that is known to effect resuscitation.

45 Claims, 19 Drawing Sheets

U.S. PATENT DOCUMENTS 5,247,939 A 9/1993 Sjoquist et al.
5,275,158 A 1/1994 Lopin
5,275,572 A 1/1994 Ungs et al.
5,282,843 A 2/1994 Freeman
5,330,526 A 7/1994 Fincke et al.
5,391,187 A 2/1995 Freeman
5,402,884 A 4/1995 Gilman et al.
5,405,361 A 4/1995 Persson
5,456,710 A 10/1995 Gadsby
5,462,157 A 10/1995 Freeman et al.
5,466,244 A 11/1995 Morgan
5,484,391 A 1/1996 Buckman, Jr. et al.
5,484,452 A 1/1996 Persson
5,507,778 A 4/1996 Freeman
5,520,683 A 5/1996 Subramaniam et al.
5,562,710 A 10/1996 Olsen et al.
5,579,919 A 12/1996 Gilman et al.
5,591,213 A 1/1997 Morgan
5,593,427 A 1/1997 Gliner et al.
5,601,610 A 2/1997 Persson
5,611,815 A 3/1997 Cole et al.
5,617,853 A 4/1997 Morgan
5,620,465 A 4/1997 Olson et al.
5,645,571 A 7/1997 Olson et al.
5,650,750 A 7/1997 Leyde et al.
5,680,864 A 10/1997 Morgan et al.
5,683,423 A 11/1997 Post
5,697,955 A 12/1997 Stolte
5,697,960 A 12/1997 Molin et al.
5,716,380 A 2/1998 Yerkovich et al.
5,735,879 A 4/1998 Gliner et al.
5,741,305 A 4/1998 Vincent et al.
5,743,864 A 4/1998 Baldwin, II
5,749,905 A 5/1998 Gliner et al.
5,782,878 A 7/1998 Morgan et al.
5,792,190 A 8/1998 Olson et al.
5,797,969 A 8/1998 Olson et al.
5,817,151 A 10/1998 Olson et al.
5,836,993 A 11/1998 Cole
5,838,244 A 11/1998 Schmidt et al.
5,850,920 A 12/1998 Gilman et al.
5,853,292 A 12/1998 Eggert et al.
5,984,102 A 11/1999 Tay
6,075,369 A 6/2000 Morgan
6,090,056 A * 7/2000 Bystrom et al. ..... 601/41
6,178,357 B1 * 1/2001 Gliner et al. ..... 607/142
6,213,960 B1 * 4/2001 Sherman et al. ..... 601/41

* cited by examiner (Amended)

RESCUE SWITCH LIGHT 19
MAINTENANCE INDICATOR 20
DIAGNOSTIC DISPLAY 36
RESCUE SWITCH 18
70
34
SPEAKER
94
VOICE
96
76
77
78
PROGRAM MEMORY
DATA MEMORY
EVENT STORAGE MEMORY
ALARM
74
PROCESSOR AND CONTROL LOGIC
ADDRESS/DATA BUS
SERIAL PORT 42
REAL TIME CLOCK
79
92
90
88
WATCH DOG
ON/OFF
POWER CONTROL
84
POWER GENERATION
+5V
-5V
+3.3V
+12V
80

AED WITH FORCE SENSOR

Matter enclosed in heavy brackets [ ] appears in the original patent but forms no part of this reissue specification; matter printed in italics indicates the additions made by reissue.

TECHNICAL FIELD

The present invention relates to devices useful for assisting in the administration of cardiopulmonary resuscitation (CPR). More particularly, the present invention relates to a sensor for being disposed on the body of a victim to measure parameters related to the CPR.

BACKGROUND OF THE INVENTION

CPR is a technique used by a rescuer in an emergency situation to get oxygen into a victims blood when that persons heart has stopped beating and/or they are not breathing spontaneously. When performing CPR the rescuer creates blood circulation in the victims body by periodically compressing the victims chest.

The American Heart Association (AHA) recommends that the rescuer press down on the sternum with a force sufficient to depress it between 4 and 5 cm. The recommended rate for these periodic depressions is 100 times a minute (ILCOR Advisory Statement for Single-Rescuer Adult Basic Life Support). Chest compressions produce blood circulation as the result of a generalized increase in intrathoracic pressure and/or direct compression of the heart. The guidelines state "Blood circulated to the lungs by chest compressions will likely receive enough oxygen to maintain life when the compressions are accompanied by properly performed rescue breathing." A victim can be kept alive using CPR provided the rescuer(s) are able to continue delivering properly performed chest compressions and rescue breaths.

Administering chest compressions and rescue breaths is a very physically demanding task. The quality of chest compressions and rescue breaths delivered can degrade as rescuers become fatigued. When a rescuer is fatigued they may not realize that they are compressing the chest with inadequate force.

Administering CPR is a very physically demanding procedure which is performed under stressful (i.e. life and death) circumstances. Under these circumstances, the rescuer is given the difficult tasks of estimating the time between compression's, and the distance which the chest is being compressed. Much of the difficulty in estimating the distance which the chest is being compressed stems from the relative position of the rescuer and the victim. When performing chest compression's, the rescuer positions his or her shoulders directly above the victim's chest, and pushes straight down on the sternum. In this position, the rescuer's line of sight is straight down at the victim's chest. With this line of sight, the rescuer has no visual reference point to use as a basis for estimating the distance that he or she is compressing the chest.

For this reason, there is a need in the art for a practical device which provides the rescuer with feedback to indicate that the rescuer is using proper compression force and that the rate of compressions is correct. A device of this type will provide rescuers with coaching which will enable them to deliver chest compressions consistently and beneficently. To be practical, this device should be one which is already at the rescue scene so that the rescuer is not required to bring an additional piece of equipment to the scene.

Because AEDs are being widely deployed, they are often present at a rescue scene. Prior art AEDs are only capable of defibrillation. There is a need in the industry for an AED which is capable of aiding a rescuer in administering proper chest compressions to a victim.

SUMMARY OF THE INVENTION

The present invention is an AED which is capable of detecting when a rescuer is performing CPR on a victim. This AED is also capable of providing a rescuer with helpful voice prompts to coach them through a CPR procedure. Rescuers who are trained in the use of AEDs are also trained in cardiopulmonary resuscitation (CPR) and will be able to make ready use of the AED of the present invention. AEDs are presently being widely deployed, and they are often on the scene when CPR is administered.

The present invention substantially meets the aforementioned needs. The present invention provides a sensor for sensing both the force applied to the victim's chest and the frequency with which the compressions are applied in order to assist a rescuer in resuscitating a stricken victim. Feedback, preferably by means of voice prompts, is provided to the rescuer by an emergency electronic device in communication with the sensor in order to optimally time the administration of chest compressions and to deliver a chest compression that provides an optimal amount of compression of the chest.

The present invention is a force sensor, for use in combination with an automated electronic defibrillator (AED), includes a first conductive layer. A second conductive layer is spaced apart from the first conductive layer such that no electrical communication occurs between the first and second conductive layers. Electrical communication means are provided for establishing an electrical communication path between the first and second conductive layers responsive to the application of a force to said electrical communication means.

The present invention includes a method of prompting a rescuer in the application of cardiopulmonary resuscitation to a victim having the steps of:

- sensing a force applied by the rescuer to the victim's sternum;
- sensing an interval between successive applications of force to the victim's sternum;
- comparing the force applied by the rescuer to the victim's sternum in a standard of force known to effect resuscitation;
- providing a prompt to the rescuer that prompts the rescuer to vary the force delivered to approximate the force that is known to effect resuscitation;
- comparing the interval between successive applications of force to the victim's sternum to a standard interval known to effect resuscitation; and
- providing a prompt to the rescuer that prompts the rescuer to vary the interval of force application to approximate the interval that is known to effect resuscitation.

DETAILED DESCRIPTION OF THE DRAWINGS

Figure 1:
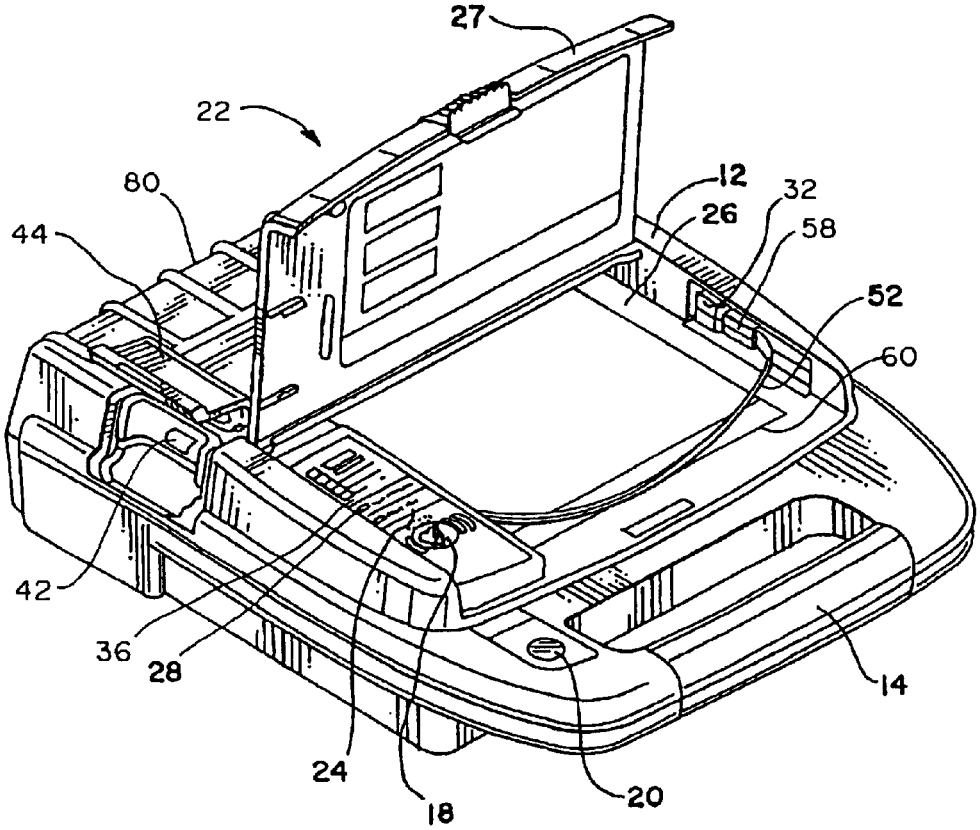
Fig. 1 PRIOR ART
FIG. 1 is a perspective view of an automated external defibrillator.

An AED is shown generally at 22 in FIG. 1. AED 22 is used for emergency treatment of victims of cardiac arrest and is typically used by first responders. AED 22 automatically analyzes a patient's cardiac electrical signal and advises the user to shock a patient upon detection of (1) ventricular fibrillation; (2) ventricular tachycardia; (3) other cardiac rhythms with ventricular rates exceeding 180 beats per minute and having amplitudes of at [lease] *least* 0.15 millivolts. When such a condition is detected, AED 22 will build up an electrical charge for delivery to the patient to defibrillate the patient with a defibrillation shock. The operator of AED 22 is guided by voice prompts and an illuminated rescue (shock) button. Olson, et al. U.S. Pat. No. 5,645,571, incorporated herein by reference, discloses the general construction and manner of use of an AED.

AED 22 includes case 12 with carrying handle 14 and battery 80, the battery 80 being removably disposed within a battery compartment (not shown) defined in case 12. Battery 80 functions as an energy source for AED 22. Visual maintenance indicator 20 and data access door 44 are located on the outside of case 12 to facilitate access by the operator. A data communication serial port 42 is situated behind data access door 44. Case 12 also includes panel 24 and electrode compartment 26 defined in a top portion thereof. Panel 24 includes illuminable rescue switch 18 and diagnostic display panel 36 with "electrodes" indicator light 28. Panel 24 and electrode compartment 26 are enclosed by selectively closeable lid 27.

Electrode compartment 26 contains connector 32 and electrode package 60. Electrode compartment 26 hermetically encloses a patient interface which includes a pair of electrodes 50 depicted in FIG. 2, and a force sensor 200, FIGS. 4–16. Electrodes 50 and force sensor 200 are removably connected to connector 32 by lead wires 52 and lead wire connector 58. Electrodes 50 are attachable to a patient prior to a rescue intervention procedure with AED 22.

AED 22 also includes a digital microprocessor-based electrical control system (see the block diagram of FIG. 3) for controlling overall operation of AED 22 and for delivering a defibrillation shock pulse through electrodes 50 via connector 32 and lead wires 52. The electrical control system further includes an impedance measuring circuit for testing the interconnection and operability of electrodes 50 to detect several faults. For example, if the conductive hydrogel adhesive on electrodes 50 is too dry or if electrodes 50 are not properly connected to connector 32 a relatively high impedance (e.g. greater than about 20 ohms) will be present across connector 32. However, when fresh electrodes 50 are properly connected, the impedance across connector 32 will be between about 2 and 10 ohms.

To insure operable electrodes 50, an electrode self-test is conducted (e.g., daily or upon opening lid 27) in which the interconnection and operability of electrodes 50 are checked with the impedance measuring circuit. If electrodes 50 are missing or unplugged from connector 32, if electrodes 50 are damaged, or if the conductive hydrogel adhesive on electrodes 50 is too dry, the control system of AED 22 will illuminate "Electrodes" indicator light 28 on diagnostic display panel 36.

*Defibrillator 22 also includes electrocardiogram (EKG) filter and amplifier 104 which is connected between elec-*

*trode connector 32 and A/D converter 102. The EKG or cardiac rhythm of the patient is processed by filter and amplifier 104 in a conventional manner, and digitized by A/D converter 102 before being coupled to processor 74.*

*The rescue mode operation of defibrillator 22 is initiated when an operator opens lid 27 to access the electrode package 60. The opening of the lid 27 is detected by lid switch 90, which effectively functions as an on/off switch. In response to this action, power control circuit 88 activates power generation circuit 84 and initiates rescue mode operation of processor 74. Processor 74 then begins its rescue mode operation and initiates the generation of an audible voice prompt "To attempt a rescue, disconnect charger." if a charger is connected when lid 27 is opened.*

*If the lid-opened self-test is successfully completed, processor 74 initiates the generation of an audible "Place electrodes." voice prompt. In response to this voice prompt, and following the instructions on the inside of lid 27, the operator should remove electrode package 60 from compartment 26, open the package, peel electrodes 50 from the release liner and place the electrodes on the patient's chest. While this action is being performed, processor 74 monitors the impedance signals received through A/D converter 102 to determine whether the impedance across the electrodes indicates that they have been properly positioned on the patient. If the correct impedance is not measured, processor 74 initiates the generation of a "Check electrodes." voice prompt.*

*After detecting an impedance indicating the proper placement of electrodes 50, and without further action by the operator (i.e., automatically), processor 74 begins a first analyze sequence by initiating the generation of a "Do not touch patient. Analyzing rhythm." voice prompt, and analyzing the patient's cardiac rhythm. In one embodiment, processor 74 collects and analyzes a nine second segment of the patient's cardiac rhythm. The cardiac rhythm analysis program executed by processor 74 is stored in program memory 76. Algorithms of the type implemented by the rhythm analysis program are generally known and disclosed, for example, in the W. A. Tacker Jr. book Defibrillation of the Heart, 1994. If the processor 74 determines that the patient has a nonshockable cardiac rhythm that is not susceptible to treatment by defibrillation pulses (e.g., no pulse rather than a fibrillating rhythm), it initiates the generation of a "Check pulse. If no pulse, give CPR." voice prompt. One minute after this voice prompt, processor 74 repeats the initiation of the "Do not touch patient. Analyzing rhythm." voice prompt and the associated cardiac rhythm analysis.*

*When a shockable cardiac rhythm is detected, processor 74 begins a first charge sequence by initiating the generation of a "Charging." voice prompt, and causes high voltage generation circuit 86 to operate in the charge mode. When the high voltage generation circuit 86 is charged, processor 74 begins a first shock sequence by initiating the generation of a "Stand clear. Push flashing button to rescue." voice prompt, and the flashing illumination of rescue switch 18. The operator actuation of rescue switch 18 will then cause processor 74 to operate high voltage generation circuit 86 in the discharge mode, and results in the application of a defibrillation pulse to the patient to complete the first series of analyze/charge/shock sequences. In one embodiment, the first defibrillation pulse delivered by defibrillator 22 has an energy content of about two hundred joules.*

*Following the first series of analyze/charge/shock sequences, processor 74 times out a short pause of about five seconds to allow the heart to reestablish its cardiac rhythm before beginning a second series of analyze/charge/shock sequences. The second series of analyze/charge/shock sequences is identical to the first series described above, except the energy content of the defibrillation pulse can be about two hundred joules or three hundred joules. If the second series of analyze/charge/shock sequences ends with the delivery of a defibrillation pulse, processor 74 again times out a short pause of about five seconds before beginning a third analyze/charge/shock sequence. The third series is also identical to the first series, but processor 74 controls the high voltage generation circuit 86 in such a manner as to cause the defibrillation pulse delivered upon the actuation of the rescue switch 18 to have an energy content of about three hundred and sixty joules.*

*Following the delivery of a defibrillation pulse at the end of the third series of analyze/charge/shock sequences, or after identifying a nonshockable cardiac rhythm, processor 74 initiates the generation of a "Check Pulse. If no pulse, give CPR." voice prompt. Processor 74 then times a one minute CPR period to complete a first set of three series of analyze/charge/shock sequences. Rescue mode operation then continues with additional sets of three series of analyze/charge/shock sequences of the type described above (all with three hundred and sixty joule pulses). Processor 74 ends rescue mode operation of defibrillator 22 when a total of nine series of analyze/charge/shock sequences have been performed, or lid 27 is closed.*

*Throughout the analyze, charge and shock sequences, processor 74 monitors the impedance present across connector 32 to determine whether electrodes 50 remain properly positioned on the patient. If the monitored impedance is out of range (e.g., too high if the electrodes have come off the patient, or too low is shortened), processor 74 initiates the generation of a "Check Electrodes." voice prompt, and causes high voltage generation circuit 86 to discharge any charge that may be present through internal load 98. Rescue mode operation will resume when processor 74 determines that the electrodes have been properly repositioned on the patient.*

Figure 2:
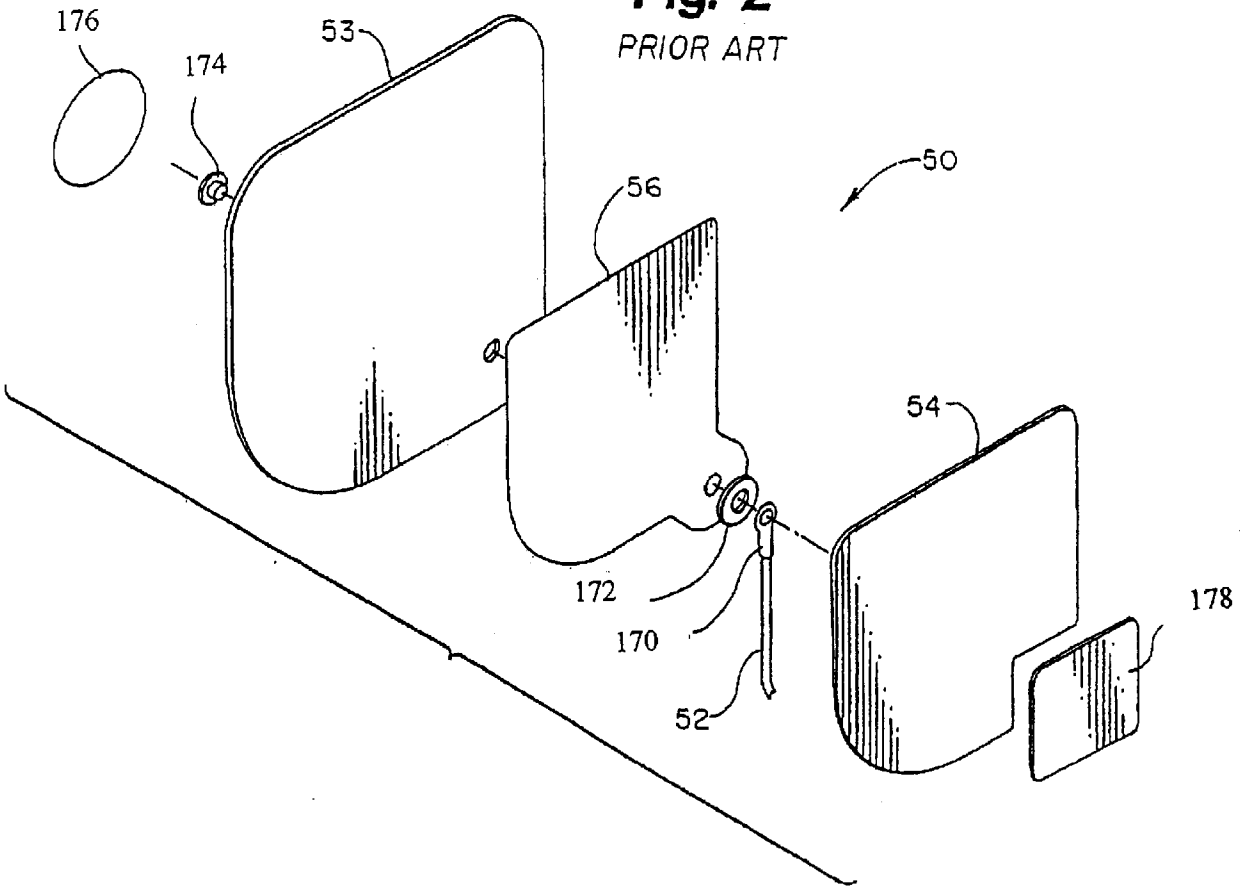
Fig. 2 PRIOR ART
FIG. 2 is an exploded view of an electrode having the force sensor of the present invention.

FIG. 2 is an exploded view of a prior art electrode 50. Electrode 50 includes flexible, adhesive coated backing layer 53 (preferably a polymeric foam), and patient engaging layer 54. Patient engaging layer 54 is preferably a hydrogel material which has adhesive properties and which is electrically conductive. Hydrogel adhesive of this type is commercially available from LccTcc Corporation (Minnetonka, Minn.) and Tyco International Ltd. (Hamilton, Bermuda). Current disbursing flexible conductive portion 56 is preferably located between backing layer 53 and patient-engaging hydrogel layer 54. Conductive portion 56, as shown, need not be the same size as backing layer 53 and is preferably a homogeneous, solid, thinly deposited metallic substance, or a conductive ink.

Insulated lead wire 52 is terminated with a wire terminal *1*70. Wire terminal *1*70 is electrically connected to conductive portion 56 via conductive rivet *1*74 and washer *1*72. Conductive rivet *1*74 is covered on a first side with insulating disk *1*76. Conductive rivet *1*74, washer *1*72, and wire terminal *1*70 are all covered on a second side with insulating pad *1*78. Further examples of electrode pad construction for use with AED 22 are described and shown in U.S. Pat. Nos. 5,697,955, 5,579,919, and 5,402,884, all hereby incorporated by reference.

Figure 20:
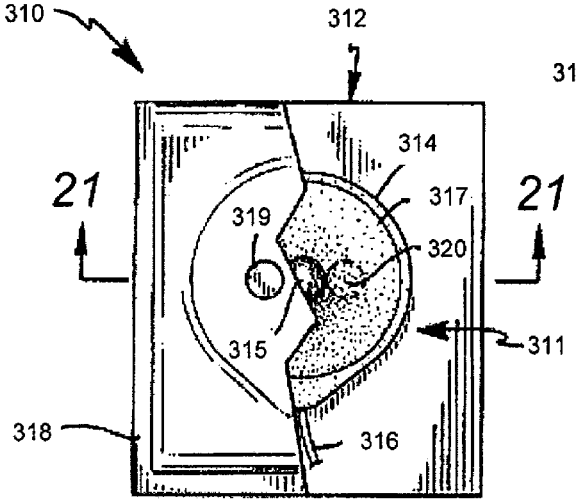
FIG. 20 is a partial cut-away view of an embodiment of a packaged electrode system.
Figure 21:
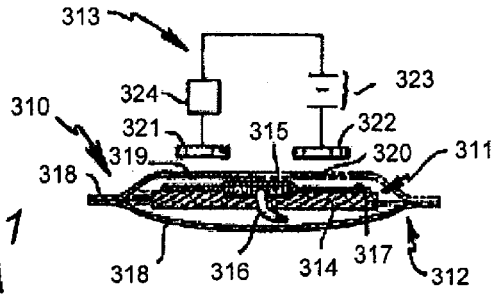
FIG. 21 is a cross-sectional view of an embodiment of a packaged electrode system and test apparatus.

*For example, referring to FIGS. 20 and 21 an embodiment of a packaged electrode system 310 is shown to comprise an electrode 311 and a package or enclosure 312. Also shown in FIG. 21 is a test apparatus 313. The electrode 311 is*

*shown to comprise a non-conductive base or backing layer 314, a conductor or conductive layer 315, a lead 316, and a conductive contact layer 317. The base layer 314 is preferably constructed of a thin, flexible polymeric substance such as a urethane foam, or a polyester or polyolefin laminate which provides structural base and insulative properties. Although the base layer 314 is shown to have a surface area which is substantially coextensive with the surface of the contact layer 317, it alternatively may be slightly larger. In such larger configurations, the base layer 314 may have a pressure sensitive adhesive disposed on its patient contact side for increased adhesion to the patient body.*

*The conductive layer 315 is shown to be disposed on the first or patient side of base layer 314. It functions to transfer (disperse) current or voltage from the lead 316 (or to the lead in a sensing application) to the patient contact layer 317. Although the conductive layer 315 is shown to have a surface area which is smaller than that of the base layer 314 or contact layer 317, it may alternatively have a dimension which is larger than that shown, or even on which is coextensive with the base and contact layers 314 and 317. The conductive layer 315 is preferably a homogeneous, solid, thinly deposited metallic substance, or a conductive ink material. Alternatively, the conductive layer 315 may be formed of a flexible mesh material, a conductive adhesive or a deposited ink pattern. Flexible conductive ink compounds known in the art have a conductive filler of Gold, Silver, Aluminum or other conductive materials.*

*The lead 316 is preferably an insulated wire conductor which extends from a mating point with the conductive layer 315, through the base layer 314, and then has a freely movable end. Various alternatives of this lead 316 design exist and are useable consistent with the general teachings of the invention, including but not limited to uninsulated wire conductors and conductive strips or traces deposited between the contact layer 317 and the base 314 or conductive layers 315. Such a trace or strip may also extend just beyond the base layer 314 for connection with an ancillary connection means such as a wiring harness including conductive clip means.*

*The conductive contact layer 317 is preferably a thin layer of semi-liquid gel material. The gel maintains direct electrical contact with the skin, to reduce variations in conductance, and it permits such contact for long periods of time. The gel is a conductive, gelatinous compound which is also flexible for contoured adhesion to the body of a patient. The gel also preferably has a pressure sensitive, moisture resistant adhesive property. Compounds having these characteristics have been developed by Minnesota Mining and Manufacturing, Medtronic, and Lec Tec (Synkara TM), Corporations, all of Minnesota, U.S.A. Generally, these compounds have low resistivities. The contact layer 317 is for direct contact with the patient's body to transfer current or voltage thereto or therefrom. Overall, although the electrode 311 and its constituent elements are shown to have circular configurations, they may alternatively be formed in various other shapes such as rectangular or square patches.*

*The package structure 312 is shown to have an envelope-like structure formed of a substantially continuous thin, homogeneous layer 318 of a polymeric, preferably non-gas permeable, material. Alternatively, as shown in FIG. 38, the package 387 embodiment may have a pouch-like structure formed of a pair of thin, flat homogeneous layers 388 and 389 which are sealed or otherwise merged together at their peripheries or outer edges 390. And, although the package 312 is shown to have a rectangular configuration various other configurations and shapes are also useable.*

Figure 35:
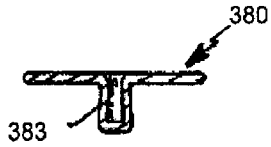
FIG. 35 is a cross-sectional view of a partial embodiment of a packaged electrode system.
Figure 36:
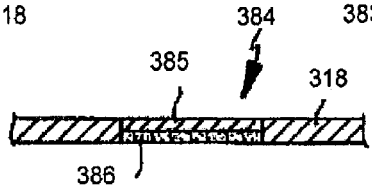
FIG. 36 is a cross-sectional view of a partial embodiment of a packaged electrode system.

*The package further comprises a pair of conductive connectors 319 and 320 which are separated a predetermined distance from one another for contact with separate areas of the contact layer 317 of the enclosed electrode 311. The connectors 319 and 320 are conductive areas which are shown to have a unitary construction with the package layer 318. The contacts 319 and 320 may alternatively be formed of thin layer strips of conductive material, or a printed conductive ink, disposed on the interior side of the package layer 318, extending from contact nodes to peripheral contact areas on the exterior of the package 318. Yet another snap-type embodiment 379 is shown in FIGS. 35 and 36 including a connective member 380 disposed on one side of the base layer 318, and a current dispersion member 381 disposed on the opposite side and being connected to the upper member 380 via an aperture in the base 318. The upper member 380 is shown 360 have a base 382 and a mating notch 383 for coupling the lower member 381.*

Figure 37:
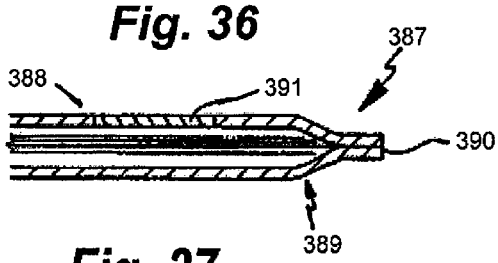
FIG. 37 is a cross-sectional view of a partial embodiment of a packaged electrode system.

*Referring to FIG. 21, the system 310 may also include a test apparatus 313. The test apparatus 313 includes a current source 323, preferably a battery, test circuitry 324, preferably including measurement components and status indication components such as an analog meter, LCD digital display or light emitting diodes, and connectors 321 and 322 for coupling with the package 312 connectors 319 and 320. In use, the test apparatus 313 is connected to the package connectors 319 and 320. The test circuitry 324 is then activated to form a closed current loop to determine whether continuity exists with respect to the enclosed electrode 311, thereby indicating whether the electrode 311 is still functional. Additionally, a load 386 formed of for example a conductive and semi-conductive material layers 385 and 386, may be added to the current loop as for example is shown in FIG. 37, for purposes of measuring the magnitude of current flow for more precise measurement of electrode 311 condition.*

*In the case of the electrode system 310, a current loop is formed including the connector 319, the gel of the contact layer 317 (along a substantially horizontal plane), and the connector 320 which is located at a remote location on the contact layer 314 with respect to the connector 319. Current conducts easily in fresh, semi-liquid gel of the contact layer 317. In contrast, no current conducts, or current conduction is attenuated, in stale, dried gel. This is indicative of the need to dispose of the stored electrode without using it. And, this condition is determinable without the need to open the package 312 and thereby risk compromising the freshness or sterility of a viable electrode 311.*

Figure 22:
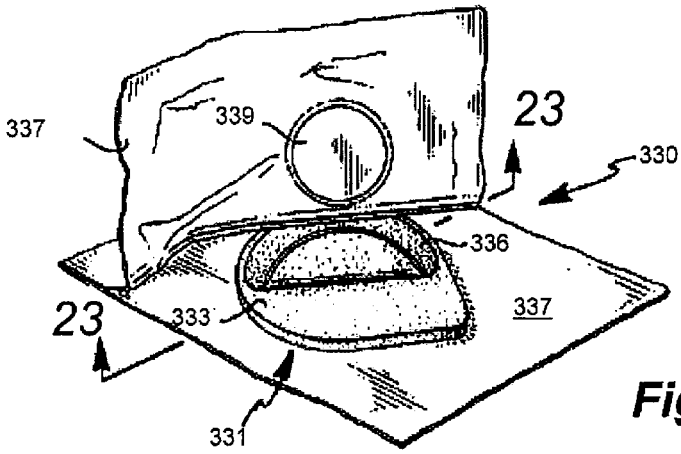
FIG. 22 is a perspective assembly view an embodiment of a packaged electrode system.
Figure 23:
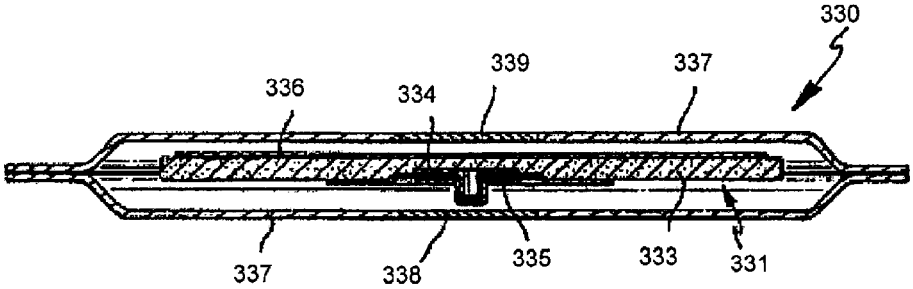
FIG. 23 is a cross sectional view of an embodiment of a packaged electrode system.

*Referring to FIGS. 22 and 23, another packaged electrode system 330 is shown to comprise an electrode 331 and a package or enclosure 332. The electrode 331 is shown to comprise a non-conductive base layer 333, and a conductive gel layer 336. A conductive snap-type connector having a connection member 335 disposed on one side and a current dispersion member 334 disposed on the second side is also shown. The package 332 is shown to have at least one body layer 337 with a pair of contacts 338 and 339 disposed at predetermined locations to electrically connect with the gel layer 336 and contact 335. In a test mode, a current loop is formed between the connector 339, gel layer 336, connector portions 334 and 335 and connector 338.*

Figure 24:
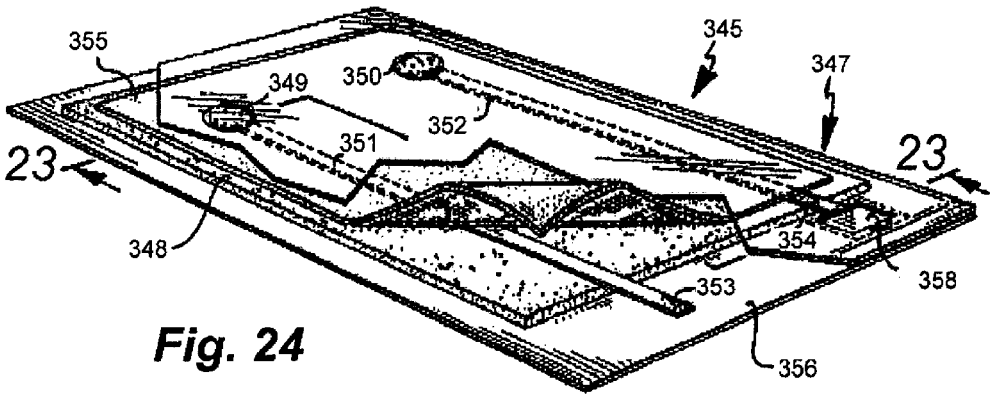
FIG. 24 is an partial cut-away view of an embodiment of a packaged electrode system.
Figure 25:
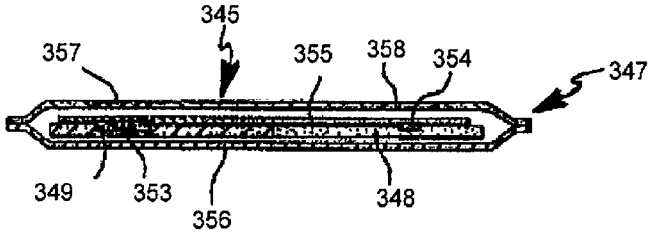
FIG. 25 is cross sectional view of an embodiment of a packaged electrode system.

*Referring to FIGS. 24 and 25, another packaged electrode system 345 is shown to comprise an electrode 346 and an enclosure 347. The electrode 346 is shown to comprise a non-conductive base layer 348, a conductive gel layer 355, and a pair of separate conductive layers 349 and 350, each of which are shown to have a lead 351 and 352 extending*

*therefrom and terminating in a connective node 353 and 354. The lead pair 351 and 352 (and layer pair 349 and 350) provide a redundant circuit path for increased reliability of use in emergency settings. The package 347 is shown to have at least one body layer 356 with a pair of contacts 357 and 358 disposed at predetermined locations to electrically couple with connective nodes 353 and 354. In a test mode, a current loop is formed between a connector 357 or 358, it's respective connective node 353 or 354 and lead 351 or 352, and its respective conductive layer 349 or 350. In a properly functioning electrode 346, current conducts through the gel 355 from one conductive layer 349 to the other 350, and then back to the test apparatus through the above-mentioned path.*

Figure 26:
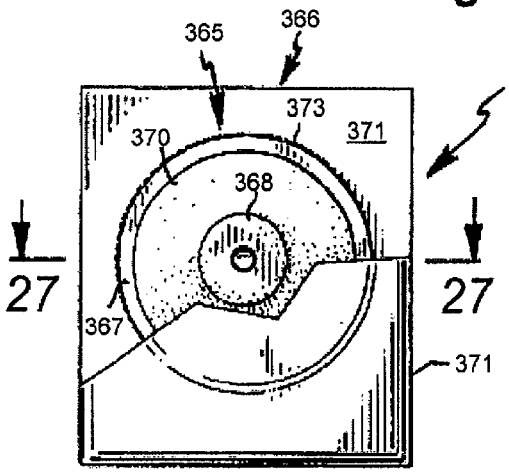
FIG. 26 is partial cut-away view of an embodiment of a packaged electrode system.
Figure 27:
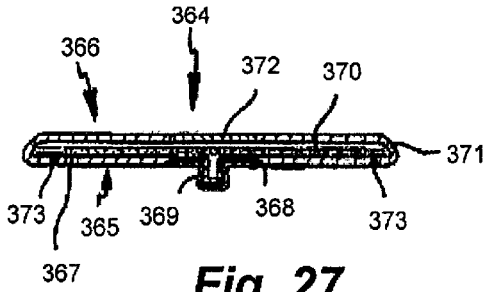
FIG. 27 is a cross-sectional view of an embodiment of a packaged electrode system.

*Referring to FIGS. 26 and 27, another packaged electrode system 364 is shown to comprise an electrode 365 and a unitary package 366. The electrode 365 is shown to compromise a non-conductive base layer 367, and a conductive gel layer 370. A snap-type connector with members 368 and 369 electrically couples the gel layer 370.*

*The package 366 is shown to have at least one body layer 371 which is coupled to the electrode 365 base layer 367 at tear-away perforated lines 373. A connector 372 is shown disposed for contact with the electrode 365 gel layer 370. In a test mode, a current loop is formed between the connector 372, the gel layer 370, and the connector members 368 and 369.*

Figure 28:
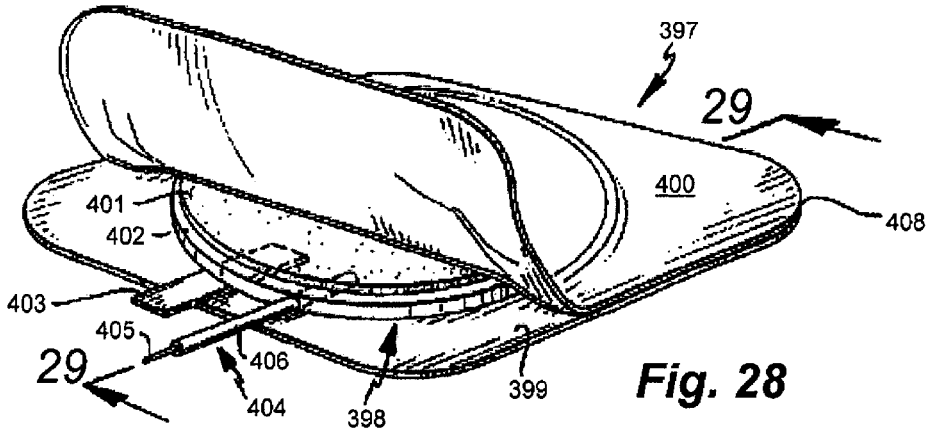
FIG. 28 is perspective assembly view an embodiment of a packaged electrode system.
Figure 29:
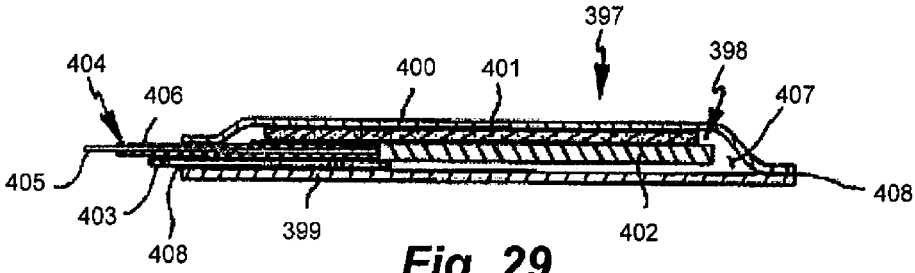
FIG. 29 is a cross-sectional view of an embodiment of a packaged electrode system.
Figure 30:
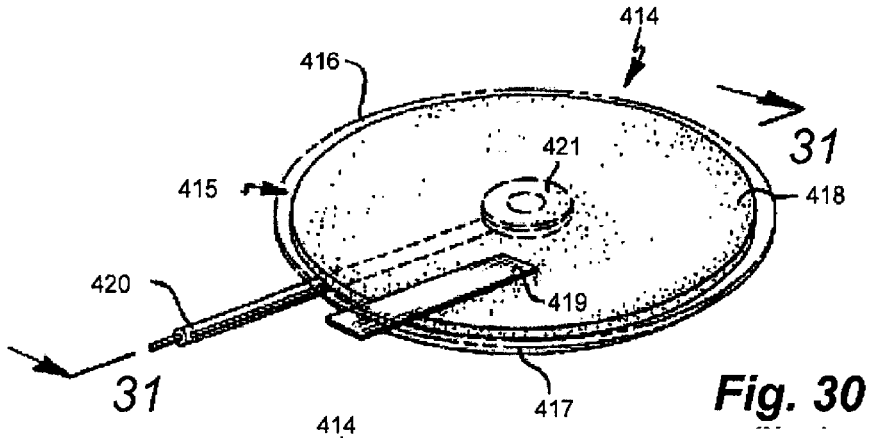
FIG. 30 is a perspective view of an embodiment of a packaged electrode system.

*Referring to FIGS. 28 and 29, another packaged electrode system 397 is shown to comprise an electrode 398 and a package. The electrode 398 is shown to comprise a non-conductive base layer 401, a conductive gel layer 402, and a lead 404 having a conductor 405 and an insulator 406, which is shown to be embedded directly in the gel layer 402. Alternatively, the lead may be connected to a conductive current dispersion layer (not shown). A conductive test strip 403 is also shown to be adhered to the surface of the gel 402 at a location remote from the lead 404 for test purposes, and which is designed to release from the gel 402 upon removal of the package layer 399.*

*The package is shown to have a pair of layers 399 and 400 which overlap to form an interior cavity 407 and area sealingly connected at their peripheries 408. In a test mode, a current loop is formed between the lead 404, the gel layer 402 and the test strip 403, which like the lead 404 is shown extended through the package periphery 408 for contact with an external test apparatus.*

Figure 31:
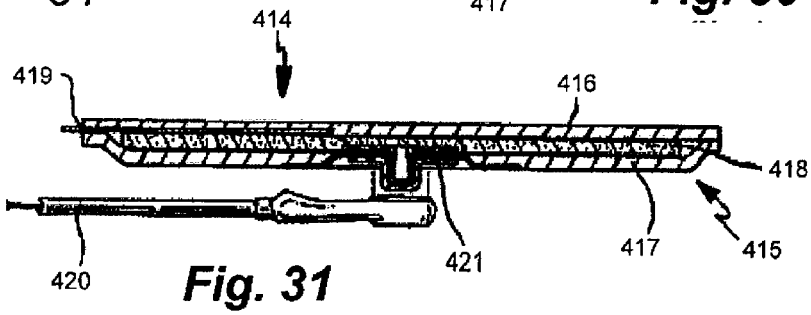
FIG. 31 is a cross-sectional view of an embodiment of a packaged electrode system.
Figure 32:
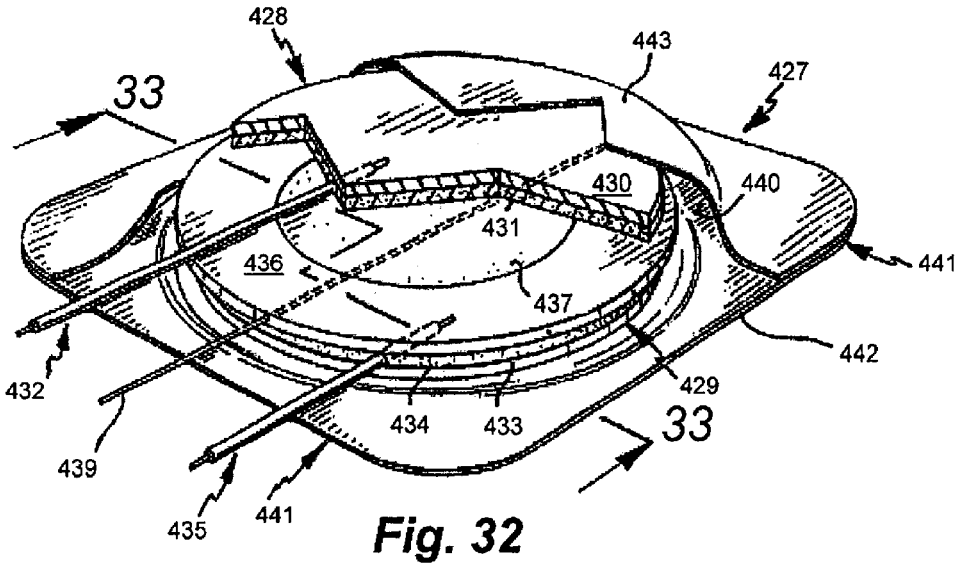
FIG. 32 is a partial cut-away view of an embodiment of a packaged electrode systsem.

*Referring to FIGS. 31 and 32, another packaged electrode system 414 is shown to comprise an electrode 415 and an enclosure. The electrode 415 is shown to comprise a non-conductive base layer 417, and a conductive adhesive gel layer 418 which is connected to a snap-type connection node 421 or the like, and an associated lead 420. The package is shown to comprise a single top layer of non-conductive material 416 which is laminated or adhesively mated to the electrode base layer 417. In use the gel layer 418 is removable from the package layer 416. A test strip 419 is disposed on the interior of the package, adhesively connected to the gel layer 418, and extending to the package exterior. In a test mode, a current loop is formed between the lead 420, node 421, gel layer 418 and the test strip 419.*

Figure 33:
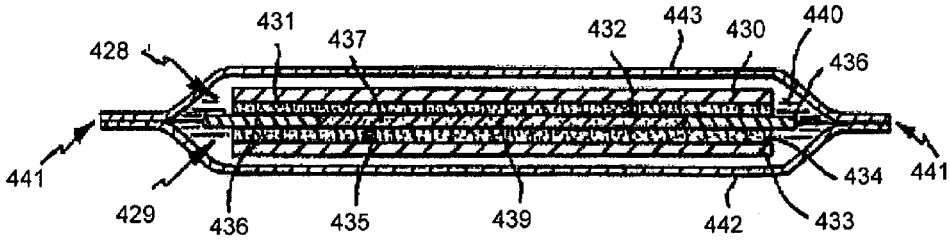
FIG. 33 is a cross-sectional view of an embodiment of a packaged electrode system.
Figure 34:
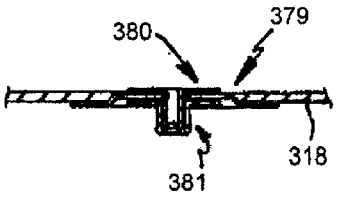
FIG. 34 is a cross-sectional view of a partial embodiment of a packaged electrode system.

*Referring to FIGS. 33 and 34, another packaged electrode system 427 is shown to comprise a pair of electrodes 428 and 429 and a package. The electrodes 428 and 429 are shown to comprise non-conductive base layers 430 and 433, and conductive gel layers 431 and 434. Leads 432 and 435 extend from the respective gel layers 431 and 434. The package is shown to have a pair of overlapping layers 442 and 443 which are sealed at their peripheries 441 to form an enclosure 440 housing the electrodes 428 and 429. Importantly, the electrodes 428 and 429 are oriented with their respective gel layers 431 and 434 mating with a resistive layer 437 (and an optional separator layer 436) formed of a conductive/resistive material as known in the art. A conductive lead 439 or strip extends from the resistive layer through the package periphery 441, as do the electrode leads 432 and 435.*

*In a test mode, a current loop is formed between, for example, a lead 432, a gel layer 431, the resistive layer 437, and the remaining gel layer 434 and lead 435. The circuit can be altered to include the lead 439.*

Figure 3A:
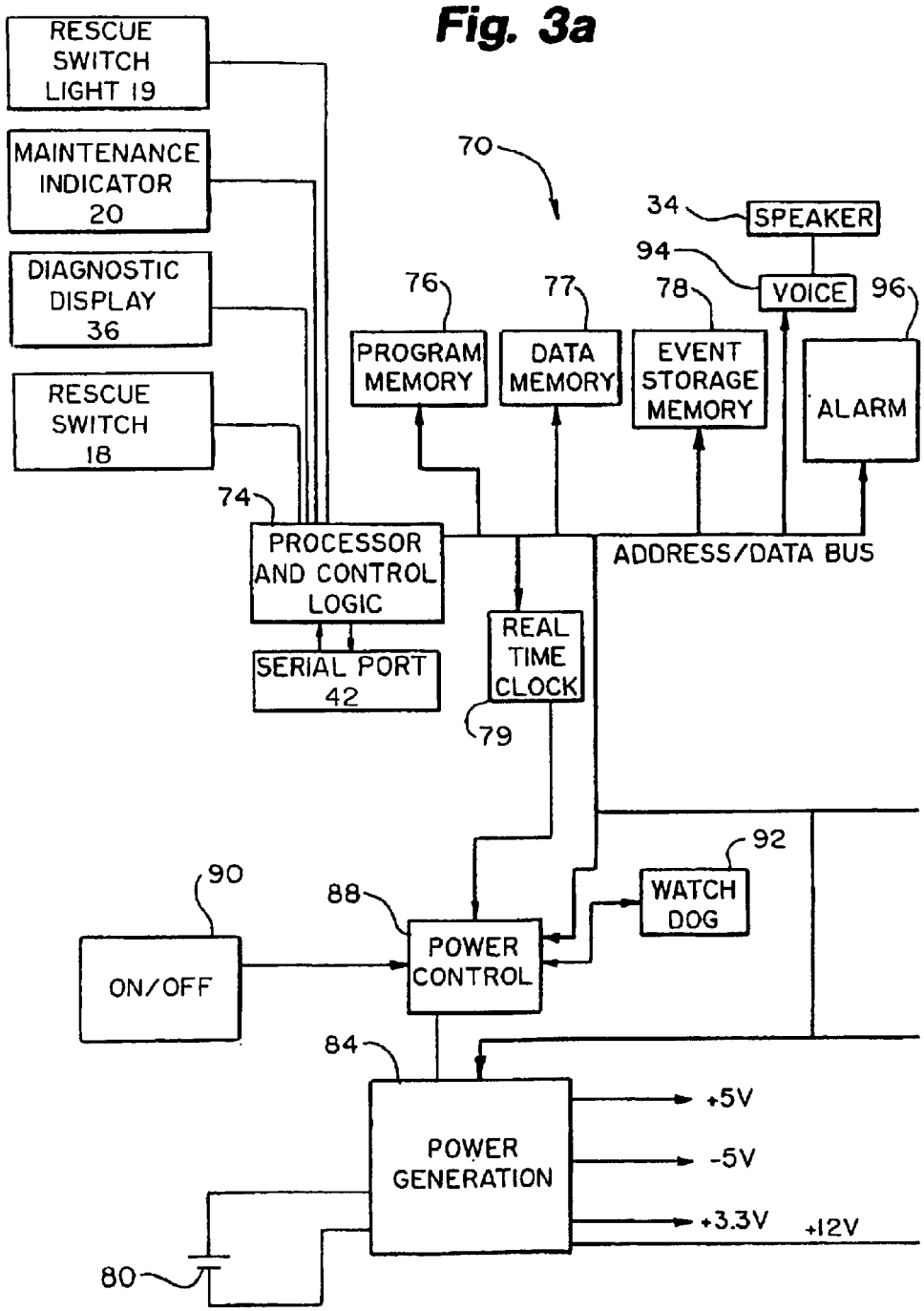
FIG. 3 is a block diagram of an electrical system of the AED.
Figure 3:
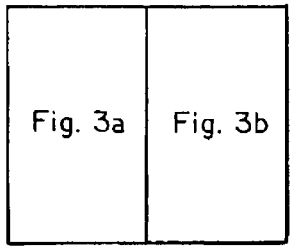
Figure 3B:
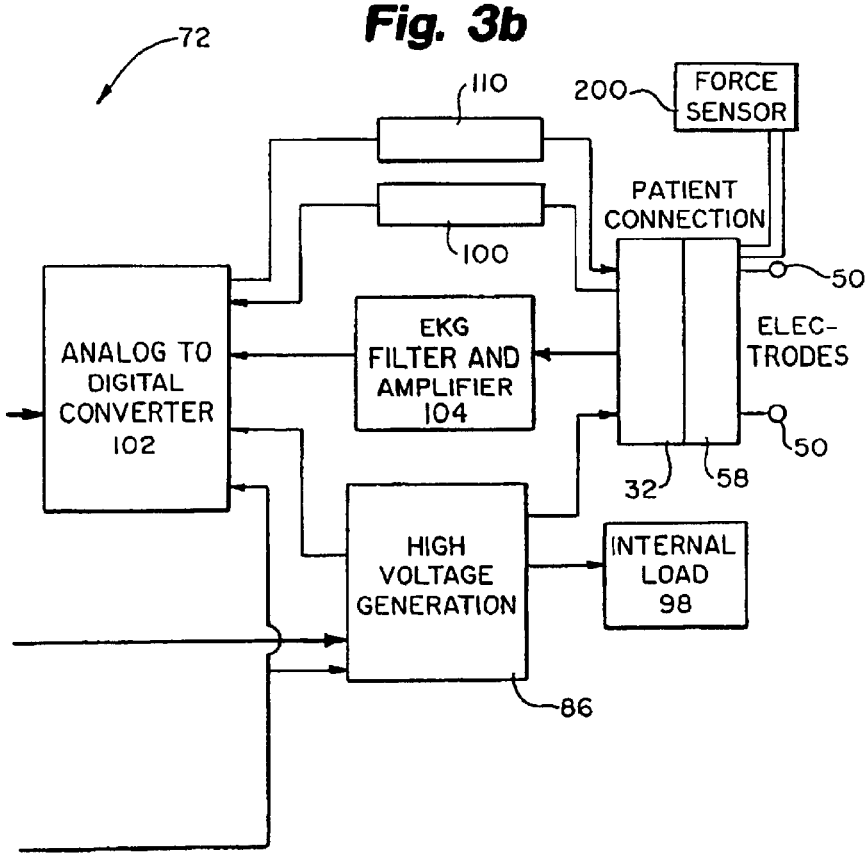

FIG. 3 is a block diagram of electrical system 70 of AED 22. The overall operation of AED 22 is controlled by a digital microprocessor-based control system 72 which includes a processor 74 interfaced to program memory 76, data memory 77, event memory 78 and real time clock 79. The operating program executed by processor 74 is stored in program memory 76. Electrical power is provided by the battery 80 which is removably positioned within the battery compartment of AED 22 and is connected to power generation circuit 84.

Power generation circuit 84 is also connected to lid switch 90, watch dog timer 92, real time clock 79 and processor 74. Lid switch 90 is a magnetic read relay switch in one embodiment, and provides signals to processor 74 indicating whether lid 27 is open or closed. Data communication port 42 is coupled to processor 74 for two-way serial data transfer using an RS-232 protocol. Rescue switch 18, maintenance indicator 20, the indicator lights of diagnostic display panel 36, the voice circuit 94 and piezoelectric audible alarm 96 are also connected to processor 74. Voice circuit 94 is connected to speaker 34. In response to voice prompt control signals from processor 74, circuit 94 and speaker 34 generate audible voice prompts for consideration by a rescuer.

High voltage generation circuit 86 is also connected to and controlled by processor 74. Circuits such as high voltage generation circuit 86 are generally known, and disclosed, for example, in the commonly assigned Persson [et al.] U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient by electrodes 50 through connector 32 connected to the high voltage generation circuit 86.

Impedance measuring circuit 100 is connected to both connector 32 and real time clock 79. Impedance measuring circuit 100 is interfaced to processor 74 through analog-to-digital (A/D) converter 102. Impedance measuring circuit 100 receives a clock signal having a predetermined magnitude from clock 79, and applies the signal to electrodes 50 through connector 32. The magnitude of the clock signal received back from electrodes 50 through connector 32 is monitored by impedance measuring circuit 100. An impedance signal representative of the impedance present across electrodes 50 is then generated by circuit 100 as a function of the ratio of the magnitudes of the applied and received clock signals (i.e., the attenuation of the applied signal).

For example, if electrodes 50 within an unopened package 60 are connected by lead wires 52 and connector 58 is properly connected to connector 32 on AED 22, a relatively low resistance (e.g., less than about 10 ohms) is present across electrodes 50. If the hydrogel adhesive 54 on electrodes 50 is too dry, or the electrodes 50 are not properly positioned on the patient, a relatively high resistance (e.g., greater than about two hundred fifty ohms) will be present across the electrodes 50. The resistance across electrodes 50 will then be between about twenty-five and two hundred fifty ohms when fresh electrodes 50 are properly positioned on the patient with good electrical contacts. It should be noted that these resistance values are given as exemplary ranges and are not meant to be absolute ranges. The impedance signal representative of the impedance measured by circuit 100 is digitized by A/D converter 102 and provided to processor 74.

Impedance measuring circuit 110 is connected to connector 32 and real time clock 79, and is interfaced to processor 74 through analog-to-digital (A/D) converter 102. Impedance measuring circuit 110 receives a clock signal having a predetermined magnitude from clock 79, and applies the signal to force sensor 200 through connector 32. The magnitude of the clock signal received back from force sensor 200 through connector 32 is monitored by impedance measuring circuit 110. An impedance signal representative of the impedance present across force sensor 200 is then generated by circuit 110 as a function of the ratio of the magnitudes of the applied and received clock signals (i.e., the attenuation of the applied signal). The impedance signal representative of the impedance measured by circuit 110 is digitized by A/D converter 102 and provided to processor 74.

Figure 4:
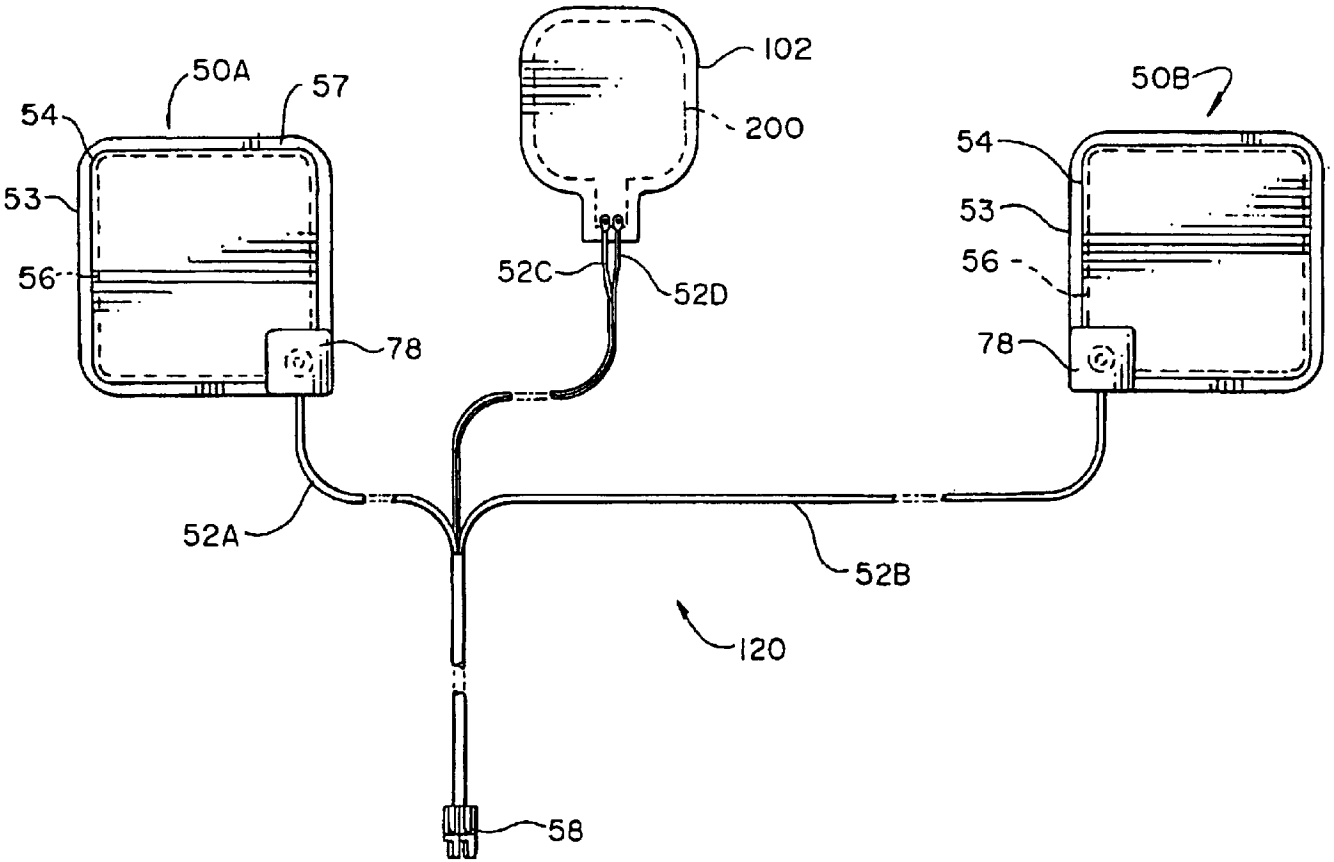
FIG. 4 is a perspective view of the force sensor used in conjunction with a pair of electrodes.

FIG. 4 is a plan view of a patient interface 120 for use with AED 22. Patient interface 120 includes connector 58 which is adapted to releasably mate with connector 32 of AED 22. Four lead wires 52A, 52B, 52C, and 52D are all terminated with connector 58. Patient interface 120 also includes a force sensing pad 102 which includes a force sensor 200. Lead wires 52C and 52D are electrically connected to force sensor 200. Electrodes 50A and 50B each include backing layer 53, patient engaging hydrogel layer 54, conductive portion 56, and insulating pad 78.

Figure 5:
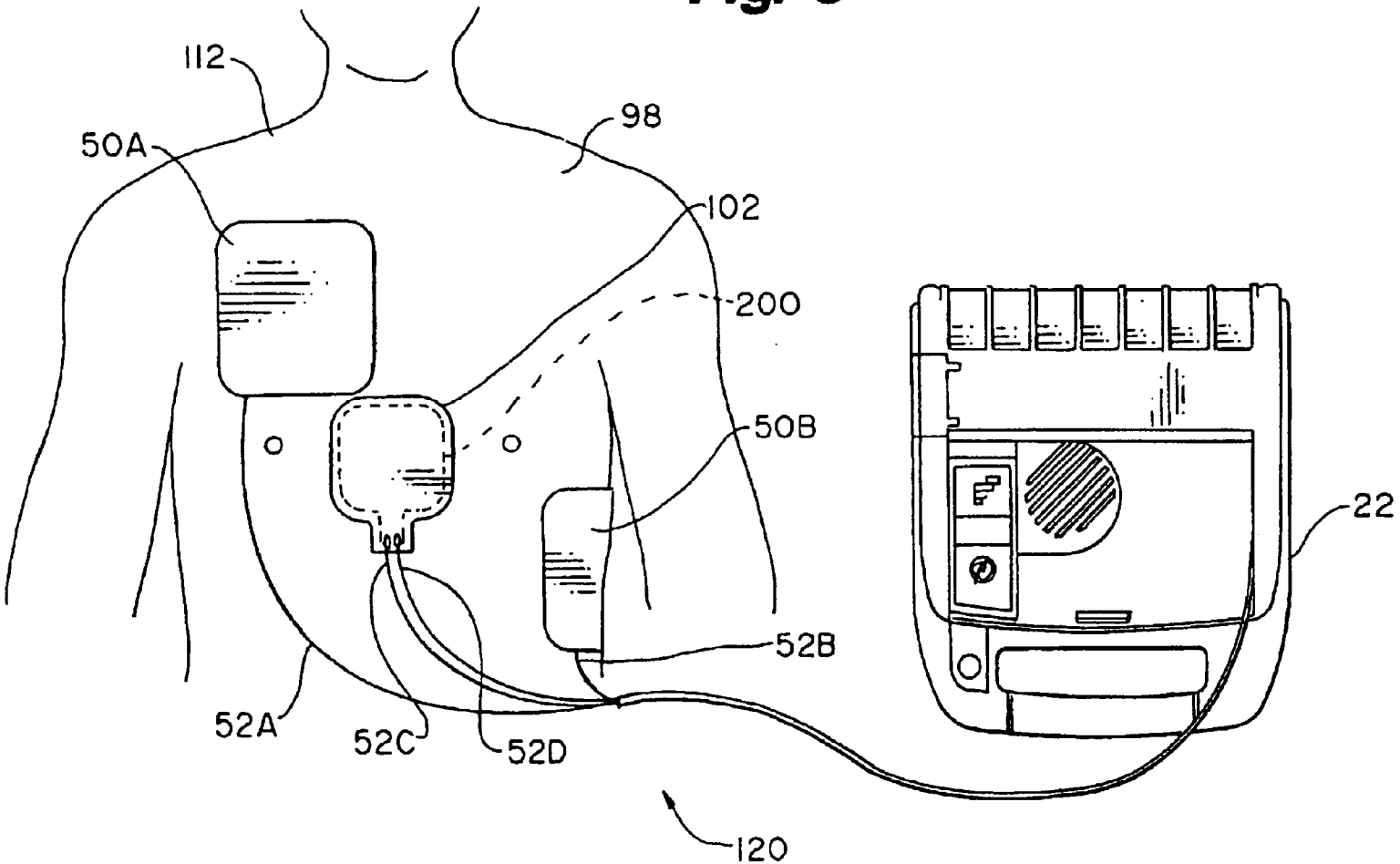
FIG. 5 is a perspective view of the force sensor of the present invention applied to a patent.

FIG. 5 is a plan view illustrating patient interface 120 applied to human torso 98 of the victim 112. Force sensing pad 102 is applied over the sternum of torso 98. Force sensing pad 102 may be adhered with pressure sensitive adhesive. Force sensing pad 102 includes force sensor 200 which is electrically connected to lead wires 52C and 52D.

Electrode 50A is shown applied to the upper right chest of torso 98. Electrode 50A is electrically connected to lead wire 52A. Electrode 50B is applied to the lower left side of torso 98 and is electrically connected to lead wire 52B. Lead wires 52A, 52B, 52C, and 52D are terminated with connector 58. Connector 58 is adapted to make releasable, electrical contact with connector 32 of AED 22.

Those skilled in the art will readily recognize that electrodes 50A, 50B and force sensing pad 102 may be placed in locations on torso 98 other than those shown in FIG. 5 without deviating from the spirit or scope of this invention.

Figure 6:
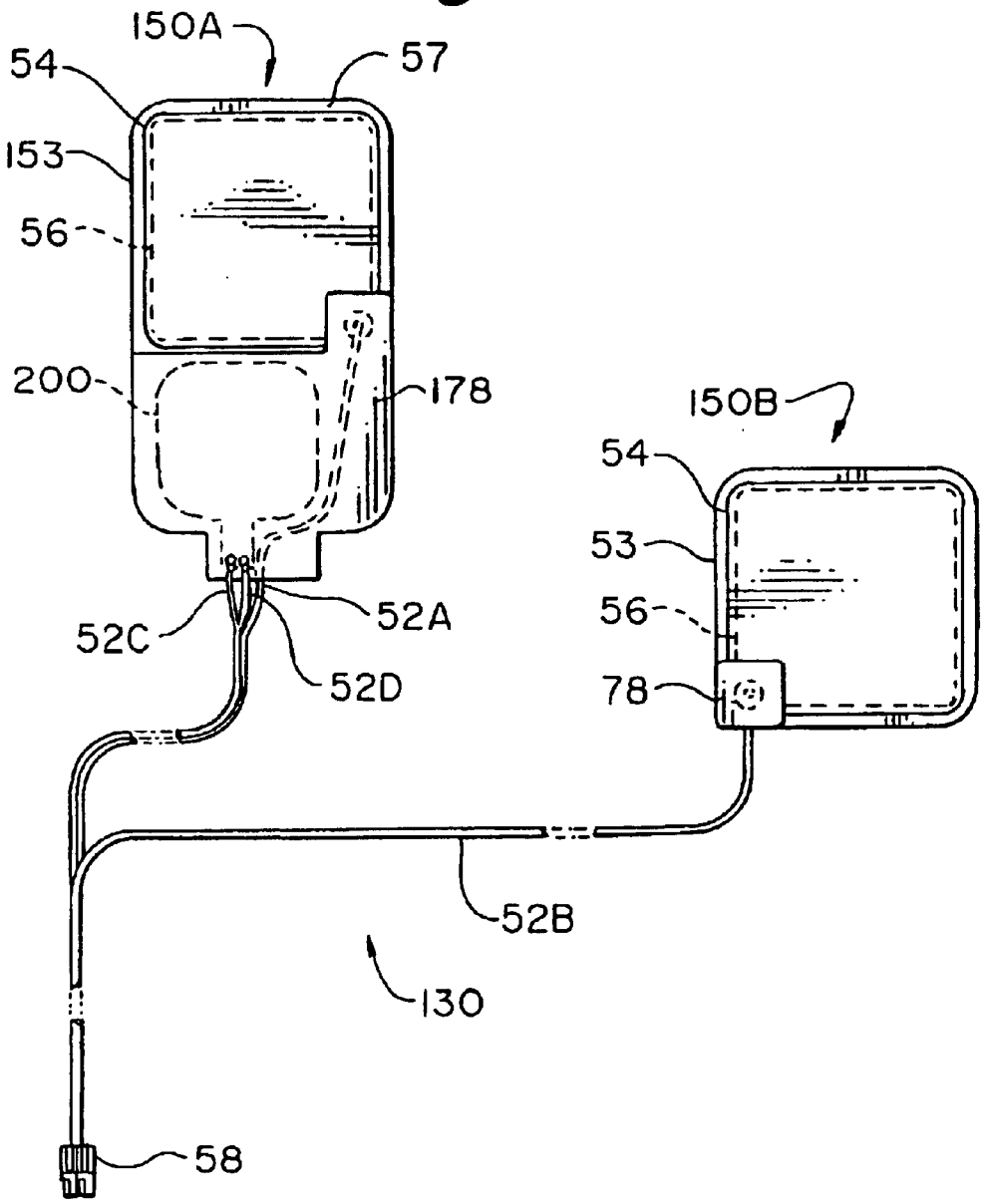
FIG. 6 is a perspective view of an electrode with the force sensor of the present invention disposed therein.

FIG. 6 is a plan view of a patient interface 130 for use with AED 22. Interface 130 includes a second preferred embodiment of force sensor 200. Patient interface 130 includes connector 58 which is adapted to releasably mate with connector 32 of AED 22. Four lead wires 52A, 52B, 52C, and 52D are all terminated with connector 58. Patient interface 130 also includes force sensor 200 which is positioned between backing layer 153 and insulating pad 178 of electrode 150A. Lead wires 52C and 52D are electrically connected to force sensor 200. Electrodes 150A and 150B each include patient engaging hydrogel layer 54, and conductive portion 56.

Figure 7:
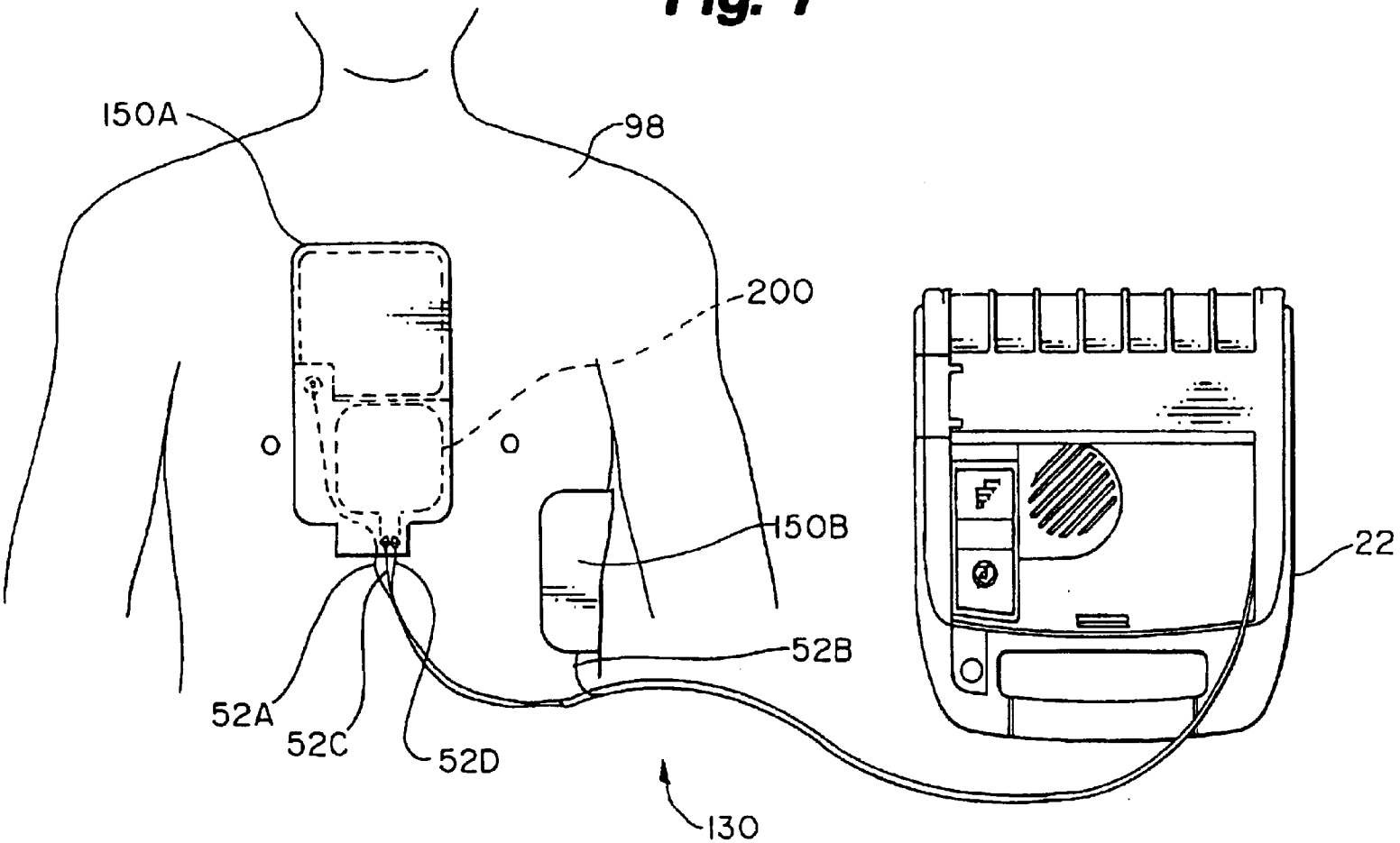
FIG. 7 is a perspective view of the force sensor of FIG. 6 applied to the chest of a victim.

FIG. 7 is a plan view illustrating patient interface 130 applied to torso 98. Force sensor 200 is positioned over the sternum of torso 98. Force sensor 200 is electrically connected to lead wires 52C and 52D. Electrode 150A is shown applied to torso 98. Electrode 150A is electrically connected to lead wire 52A. Electrode 150B is applied to the lower left side of torso 98 and is electrically connected to lead wire 52B. Lead wires 52A, 52B, 52C, and 52D are terminated with connector 58 (not shown). Connector 58 is adapted to make releasable, electrical contact with connector 32 (not shown) of AED 22.

Figure 8:
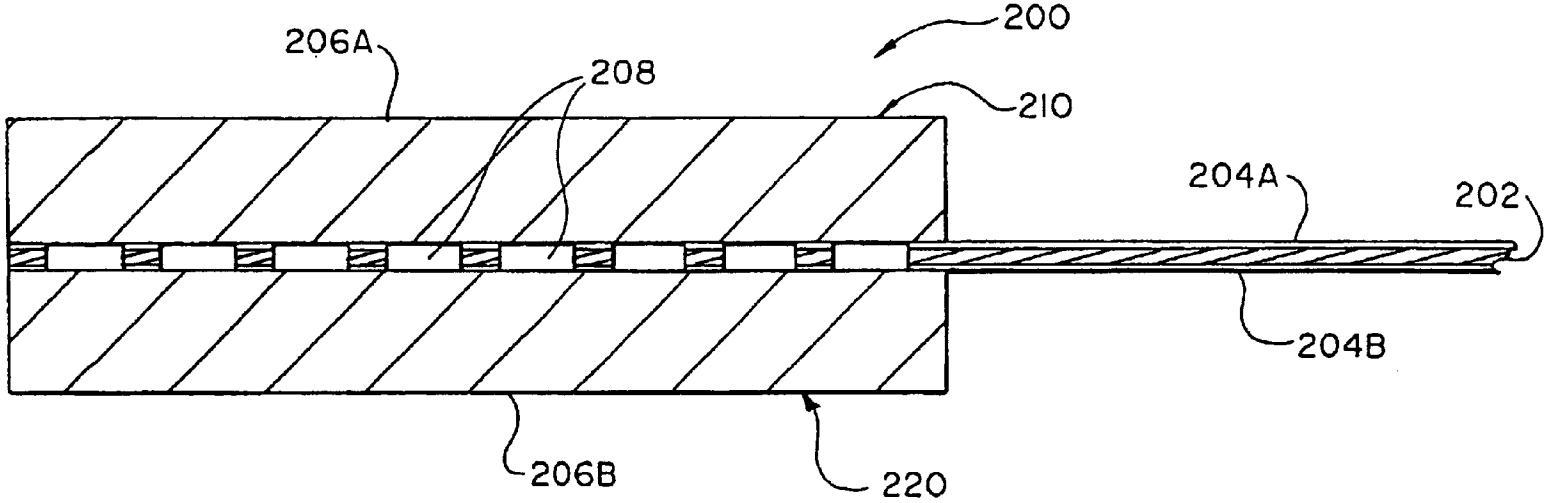
FIG. 8 is a cross sectional side view of the electrode of the present invention.

FIG. 8 is a cross section illustrating an embodiment of a force sensor 200. Force sensor 200 has a first side 210 and a second side 220. Force sensor 200 includes a substrate 202. A conductive pattern 204A, 204B is situated on each side of the substrate layer. Substrate 202 may be any thin (e.g. about 0.002" to 0.020") nonconductive sheet of material. Plastic film materials such as polyester, polycarbonate, PVC, etc. have been found to work well as substrate 202. Conductive patterns 204A, 204B may be any conductive material such as copper foil, nickel foil, or conductive ink. In a preferred embodiment substrate 202 is 5 mil polyester and conductive patterns 204A, 204B are silver conductive ink.

Substrate 202 includes apertures 208. Conductive pads 206A and 206B are situated on each side of substrate 202 as shown in FIG. 8. Conductive pads 206A, 206B are preferably made of a deformable, conductive material. Materials which have been found suitable include conductive silicone rubber, conductive foam rubber, and conductive urethane rubber.

Figure 9:
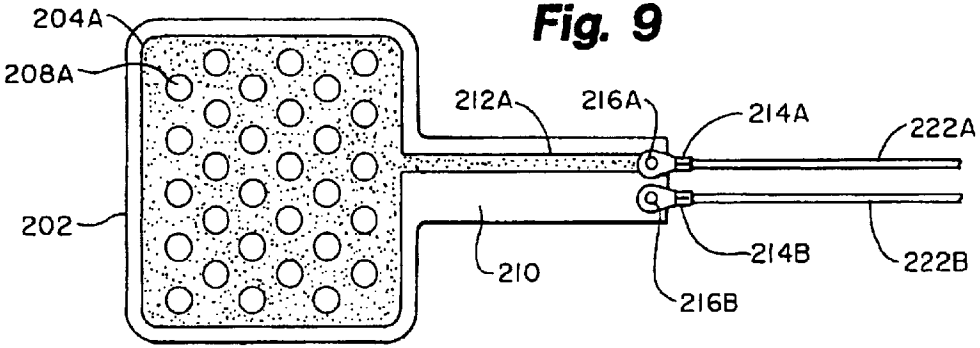
FIG. 9 is a top plan view of a further embodiment of the force sensor of the present invention.

FIG. 9 is a plan view illustrating first side 210 of force sensor 200 with conductive pads 206A, 206B removed. Conductive pattern 204A is seen situated on substrate 202. Apertures 208 are cut through conductive pattern 204A, substrate 202, and conductive pattern 204B, underlying substrate 202.

Figure 10:
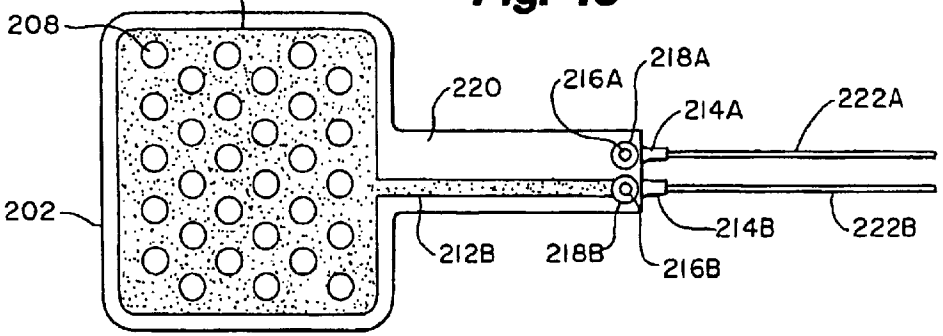
FIG. 10 is a bottom plan view of the force sensor depicted in FIG. 9.

FIG. 10 is a plan view illustrating second side 220 of force sensor 200 with conductive pads 206A, 206B removed. Conductive pattern 204B is seen situated on substrate 202. As also shown in FIG. 9, apertures 208 are cut through conductive pattern 204B, substrate 202, and conductive pattern 204A, underlying substrate 202.

Referring now to both FIG. 9 and FIG. 10, conductive patterns 204A, 204B each include conductive traces 212A, 212B. Wire terminals 214A, 214B are arranged make electrical contact with conductive traces 212A, 212B respectively. Wire terminals 214A, 214B are attached to substrate 202 with rivets 216A, 216B and washers 218A, 218B. Lead wires 222A, 222B are terminated with wire terminals 214A, 214B.

Those with skill in the art will recognize that other methods may be used to attach lead wires 222A, 222B to conductive traces 212A, 212B. Possible methods include soldering, the use of a connector designed to mate with flexible circuits, and the use of conductive adhesive.

Figure 11:
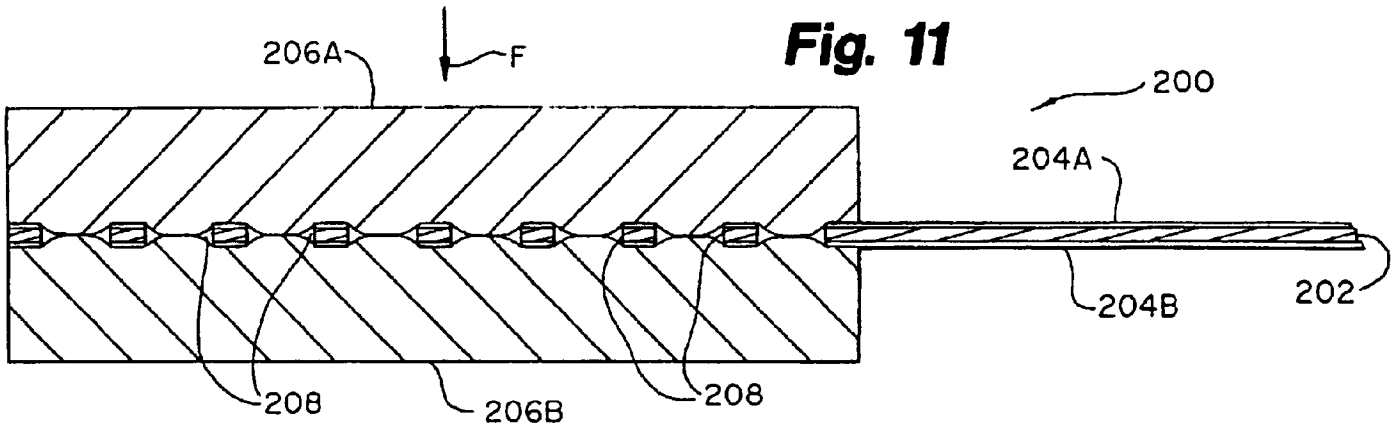
FIG. 11 is a cross sectional side view of the electrode of the present invention.

FIG. 11 is a section view of force sensor 200 with a compressive force F applied. When force sensor 200 is used, it is placed between two objects, such as the sternum of a cardiac arrest victim and the heel of a rescuer's hand. When the rescuer presses down with the heel of his or her hand, the force results in pressure distributed across the area of the heel of his or her hand.

When pressure is applied to force sensor 200, conductive pads 206A, 206B extrude through apertures 208. When pads 206A, 206B contact each other, they complete an electrical circuit between conductive layer 204A and conductive layer 204B. Increasing the force F applied to force sensor 200 increases the surface area of the electrical connection between conductive pads 206A, 206B, thereby decreasing the electrical resistance between pads 206A, 206B. The electrical resistance of the circuit between conductive layer 204A and conductive layer 204B is therefore indicative of the magnitude of the force F applied to force sensor 200.

Figure 12:
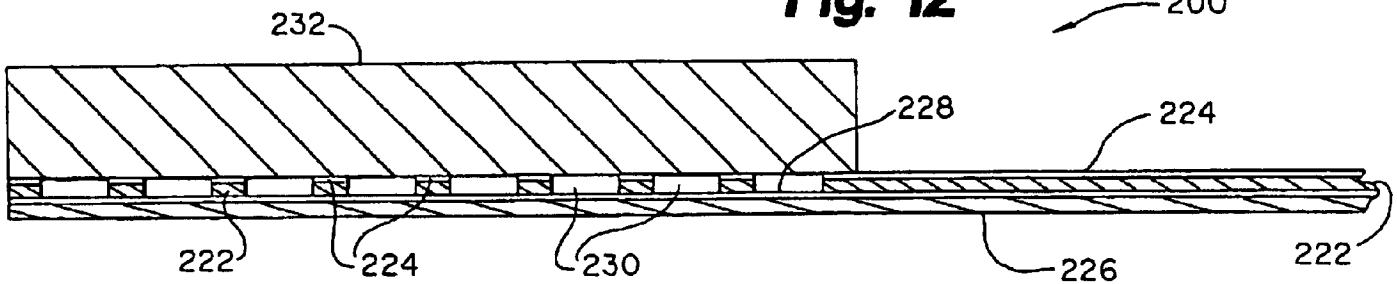
FIG. 12 is a cross sectional side view of the electrode of the present invention.
Figure 13:
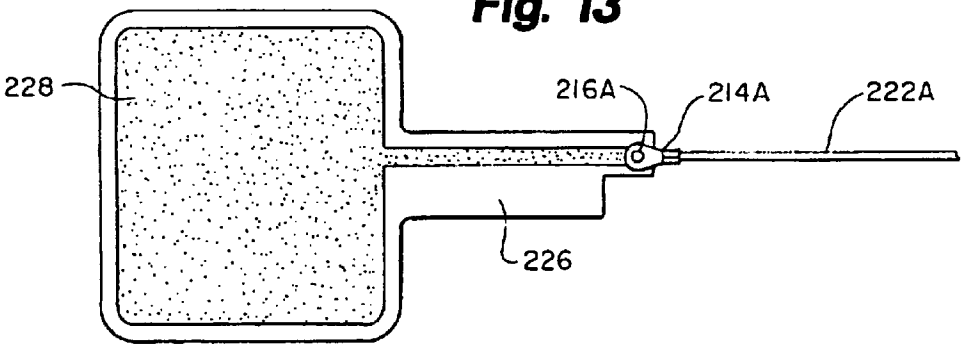
FIG. 13 is a top plan view of a further embodiment of the force sensor of the present invention.
Figure 14:
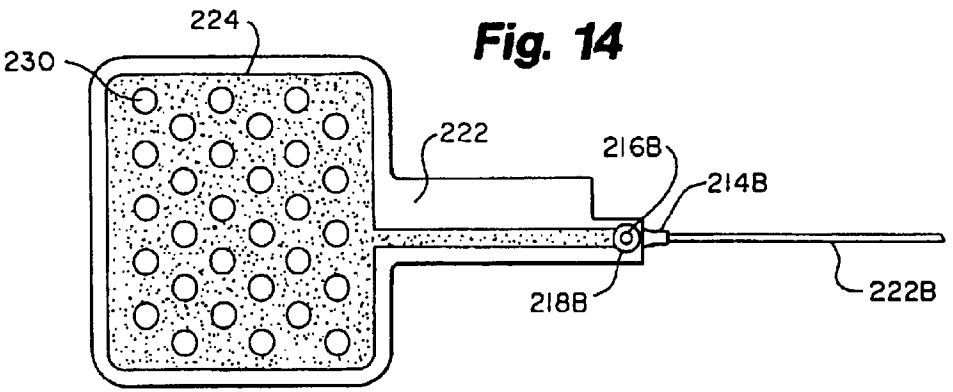
FIG. 14 is a bottom plan view of the force sensor depicted in FIG. 13.

FIGS. 12–14 illustrate a further preferred embodiment of force sensor 200. Force sensor 200 includes a first substrate 222. A conductive pattern 224 is situated on first substrate 222. As in the previous embodiment, substrate 222 may be any thin (e.g. about 0.002" to 0.010") nonconductive sheet of material. Plastic film materials such as polyester, polycarbonate, PVC, etc. have been found to work well as substrate 222. Conductive pattern 224 may be any conductive material such as copper foil, nickel foil, or conductive ink. In a preferred embodiment substrate layer 222 is 5 mil polyester and conductive pattern 224 is silver conductive ink.

Force sensor 200 includes second substrate 226. A conductive pattern 228 is situated on second substrate 226. Second substrate 226 is situated on first substrate 222. First substrate 222 and second substrate 226 may be held together with a layer of pressure sensitive adhesive (not shown).

Substrate 222 includes apertures 230. A conductive pad 232 is situated on, and makes electrical contact with conductive pattern 224 as shown in FIG. 14. Conductive pad 232 is preferably made of a deformable, conductive material. Materials which have been found suitable include conductive silicone rubber, conductive foam rubber, and conductive urethane rubber.

FIG. 13 is a plan view illustrating second substrate 226 and conductive pattern 228.

FIG. 14 is a plan view illustrating first substrate 222 and conductive pattern 224.

Figure 15:
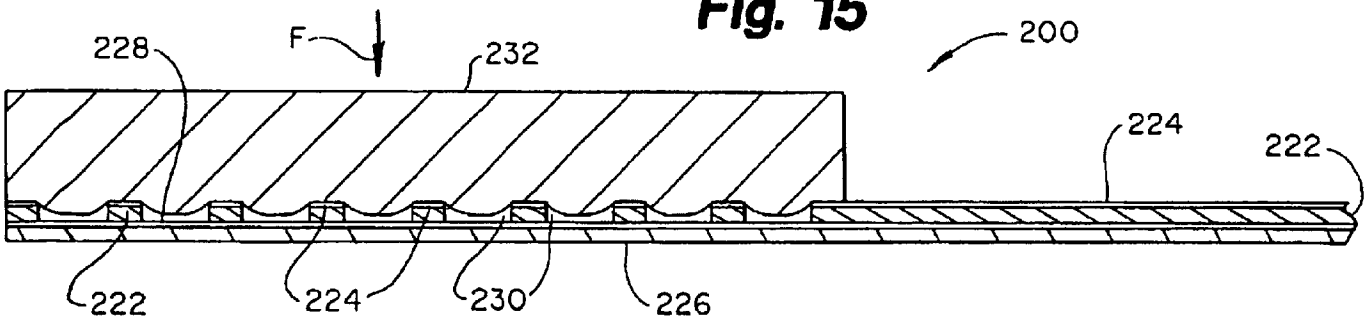
FIG. 15 is a cross sectional side view of the electrode of the present invention.

FIG. 15 is a section view of the force sensor 200 of FIG. 12 with a force F applied. When force sensor 200 is used, it is placed between two objects, such as the sternum of a cardiac arrest victim and the heel of a rescuers hand. When the rescuer presses down with the heel of his or her hand, the force results in pressure distributed across the area of the heel of his or her hand.

When a force F is applied to force sensor 200, conductive pad 232 extrudes through apertures 230. When conductive pad 232 contacts conductive pattern 228 it completes an electrical circuit between conductive pattern 224 and conductive pattern 228. Increasing the force F applied to force sensor 200 increases the surface area of the electrical connection between conductive pads 232 and conductive pattern 228, thereby reducing the electrical resistance between pad 232 and pattern 228. Accordingly, change in contact area creates a change in electrical resistance which is indicative of the force applied to force sensor 200.

Figure 16:
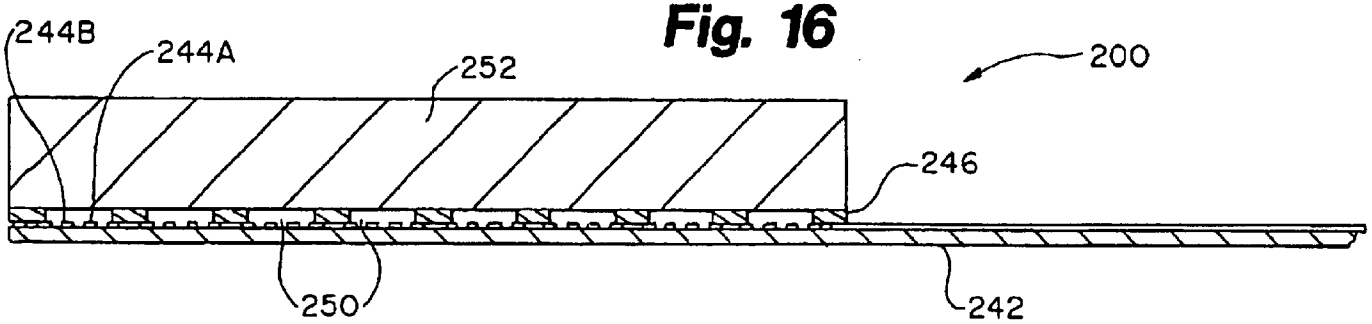
FIG. 16 is a cross sectional side view of the electrode of the present invention.
Figure 17:
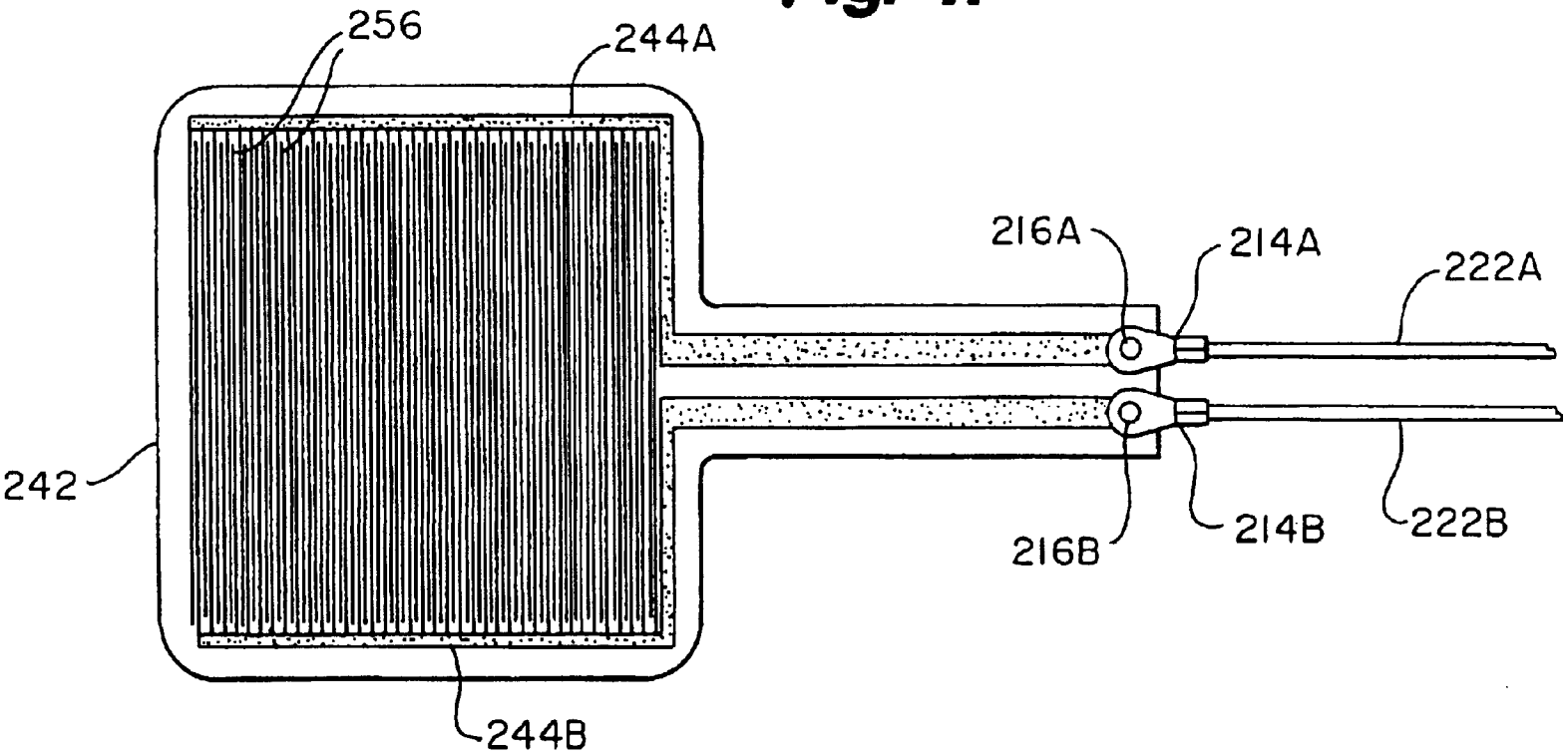
FIG. 17 is a top plan view of a further embodiment of the force sensor of the present invention.
Figure 18:
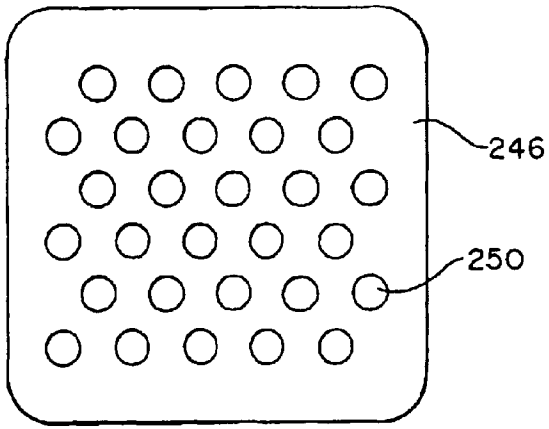
FIG. 18 is a bottom plan view of the force sensor depicted in FIG. 17.

FIGS. 16–18 illustrate another third embodiment of force sensor 200. In this embodiment force sensor 200 includes a first substrate 242. Two conductive patterns 244A, 244B are situated on first substrate 242.

Force sensor 200 includes second substrate 246 which includes apertures 250. Second substrate 246 is comprised of a non-conductive material. Polyester, polyethylene, and polypropylene have been found to be suitable materials for second substrate 246. A conductive pad 252 is situated on second substrate 246. As in the previous embodiments, conductive pad 232 is preferably made of a deformable, conductive material.

FIG. 17 is a plan view illustrating first substrate 242 and conductive patterns 244A, 244B. The conductive patterns 244A, 244B are arranged so that they are in close proximity to each other. Small gaps 256 are left between conductive paths 244A, 244B so that there is no direct electrical contact between conductive paths 244A, 244B.

FIG 18 is a plan view illustrating second substrate 246 and apertures 250.

Figure 19:
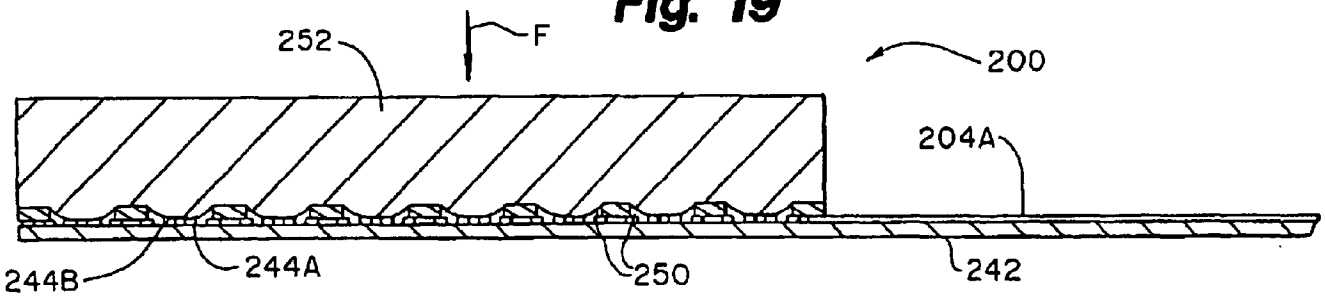
FIG. 19 is a cross sectional side view of the electrode of the present invention.

FIG. 19 is a section view of the force sensor 200 of FIGS. 16–18 with a force F applied. When force sensor 200 is used, it is placed between two objects, such as the sternum of a cardiac arrest victim and the heel of a rescuers hand. When the rescuer presses down with the heel of his or her hand, the force F results in pressure distributed across the area of the heel of his or her hand.

When pressure is applied to force sensor 200, conductive pad 252 extrudes through apparatus 250. When conductive pad 252 contacts conductive patterns 244A, 244B it completes an electrical circuit between conductive pattern 244A and conductive pattern 244B. Increasing the force applied to force sensor 200 increases the surface area of the electrical connection between conductive pad 252 and conductive patterns 244A, 244B. This change in contact area creates a change in electrical resistance which is indicative of the force applied to force sensor 200.

Referring to FIGS. 4 and 5 in operation force sensor 200 is positioned on the sternum of a victim 112. The rescuer places the heel of his or her hand onto force sensor 200 and delivers chest compressions to the chest of the victim 112. Force sensor 200 and impedance measuring circuit 110 produce an electrical signal proportional to the force applied to the victim's chest. This signal indicates to processor 74 the rate and magnitude of the chest compressions which the victim 112 is receiving. This signal also allows processor 74 to determine the precise time that a rescuer has begun (or stopped) CPR.

Processor 74 compares the measured rate of chest compressions to a range of desired values.

If the current chest compression rate value delivered by the rescuer is less than the desired range, processor 74 will produce a control signal which causes voice circuit 94 and speaker 34 to generate an appropriate voice prompt such as "faster". If the current chest compression rate value is greater than the desired range, processor 74 will produce a control signal which causes voice circuit 94 and speaker 34 to generate an appropriate voice prompt such as "slower".

Processor 74 also compares the measured chest compression force to a range of desired values. If the chest compression force delivered by the rescuer is less than the desired range, processor 74 will produce a control signal which causes voice circuit 94 and speaker 34 to generate an appropriate voice prompt such as "harder". If the chest compression force is greater than the desired range, processor will produce a control signal which causes voice circuit 94 and speaker 34 to generate an appropriate voice prompt such as "softer".

AED 22 may also provide other types of audible feedback to the rescuer. For example, AED 22 may give an audible signal each time the force measured using force sensor 200 reaches a desired value.

The present invention may be embodied in other specific forms without departing from the spirit of the essential attributes thereof. Therefore, the illustrated embodiments should be considered in all respects as illustrative and not restrictive, reference being made to the appended claims rather than to the foregoing description to indicate the scope of the invention.

What is claimed is:

1. An automated electronic defibrillator (AED) for use by an operator in assisting in resuscitating a victim, comprising:

a force sensor applicable to a skin surface of the victim and being responsive to the application of a force to said force sensor, an AED control system being in electrical communication with the force sensor, the AED control system processing a signal communicated from the force sensor related to the magnitude of force applied thereto and to the frequency of application of the force thereto; and AED prompting means operably coupled to the AED control system for receiving communication signals from the AED control system and for communicating prompts to the operator for use by the operator in resuscitating the victim, the prompts being related to the signal communicated to the AED control system by the force sensor related to the magnitude of force applied to the force sensor and to the frequency of application of the force to the force sensor.

2. The AED of claim 1 wherein the force sensor is responsive to the relative magnitude of the force applied thereto and communicates a signal related to said force magnitude to the AED control system.

3. The AED of claim 2 wherein the AED control system communicates signals relating to the relative magnitude of force applied to the force sensor to the AED prompting means for transmission as a prompt to the rescuer.

4. The AED of claim 1 wherein the AED control system determines the interval between a succession of force applications applied to the force sensor.

5. The AED of claim 4 wherein the AED control system communicates signals relating to the interval between a succession of force applications applied to the force sensor to the AED prompting means for transmission as a prompt to the rescuer.

6. The AED of claim 1 wherein the force sensor comprises:

a first conductive layer;

a second conductive layer being spaced apart from the first conductive layer, the first and second conductive layers being electrically isolated from one another; and electrical communication means for establishing electrical communication between the first and second conductive layers responsive to the application of a force to said electrical communication means.

7. The AED of claim 6 wherein at least a part of the electrical communication means of the force sensor are formed of an extrudable, electrically conductive material, the electrical communication means being extruded by the application of a force to said electrical communication means, at least one extrusion thereof establishing a path of electrical communication between the first and second conductive layers responsive to the application of said force.

8. The AED of claim 7, the force sensor further including a flexible, nonconductive layer being disposed between the first and second conductive layers.

9. The AED of claim 8 wherein the first and second conductive layers of the force sensor are formed of conductive ink printed on opposed sides of the nonconductive layer.

10. The AED of claim 9, the force sensor further including a plurality of holes defined through the nonconductive layer and through the first and second conductive layers printed thereon.

11. The AED of claim 10, the force sensor further including a first extrudable, conductive layer disposed on the first conductive layer and a second extrudable, conductive layer disposed on the second conductive layer, the first and second extrudable, conductive layers being extrudable into the plurality of holes defined through the nonconductive layer and through the first and second conductive layers responsive to a force applied thereto to form an electrically communicative connection between the first and second conductive layers.

12. The AED of claim 6 wherein the first and second conductive layers of the force sensor are formed of conductive, metallic foil.

13. The AED of claim 1 wherein the force sensor is disposed in a hole defined in an electrode.

14. The AED of claim 6 wherein the magnitude of the force applied to the force sensor is inversely proportional to the impedance existing between the first and second conductive layers.

15. The AED of claim 6 wherein the impedance existing between the first and second conductive layers of the force sensor is related to the magnitude of the force applied to the force sensor.

16. A method of prompting a rescuer in the application of cardiopulmonary resuscitation to a victim comprising the steps of:

sensing a force applied by the rescuer to the victim by means of a force sensor;

sensing an interval between successive applications of force to the victim's sternum; by means of a processor operably coupled to the force sensor, the processor comparing the force applied by the rescuer to the victim's sternum to a standard of force known to effect resuscitation;

the processor providing a prompt to the rescuer that prompts the rescuer to vary the force delivered to approximate the force that is known to effect resuscitation;

the processor comparing the interval between successive applications of force to the victim's sternum to a standard interval known to effect resuscitation; and the processor providing a prompt to the rescuer that prompts the rescuer to vary the interval of force application to approximate the interval that is known to effect resuscitation.

[17. An automated electronic defibrillator (AED) for use by an operator in assisting in resuscitating a victim, having a charging circuit for developing a high voltage charge, at least two electrodes for application to the person of a victim, the at least two electrodes being in electrical communication with the charging circuit, a control circuit communicatively coupled to the charging circuit and the electrodes for detecting certain biological parameters of the victim and for controlling the delivery of a voltage charge from the charging circuit through the at least two electrodes to the victim, comprising:

means for prompting a rescuer in the delivery of cardiopulmonary resuscitation (CPR) to the victim, the means for prompting a rescuer further including the control system being in electrical communication with a force sensor, the AED control circuit processing a signal communicated from the force sensor related to the magnitude of force applied thereto and to a frequency of application of the force thereto.]

18. The AED of claim 17 wherein the means for prompting a rescuer includes a force sensor applicable to a skin surface of the victim and being responsive to the application of a force to said force sensor.

19. [The AED of claim 17 wherein the means for prompting a rescuer] *An automated electronic defibrillator (AED) for use by operator in assisting in resuscitating a victim, having a charging circuit for developing a high voltage charge, at least two electrodes for application to the person of a victim, the at least two electrodes being in electrical communication with the charging circuit, a control circuit communicatively coupled to the charging circuit and the electrodes for detecting certain biological parameters of the victim and for controlling the delivery of a voltage charge from the charging circuit through the at least two electrodes to the victim, comprising:*

*means for prompting a rescuer in the delivery of cardiopulmonary resuscitation (CPR) to the victim, the means for prompting a rescuer including the control system being in electrical communication with a force sensor, the AED control circuit processing a signal communicated from the force sensor related to the magnitude of force applied thereto and to a frequency of application of the force thereto and* further includ[es]*ing* prompting means operably coupled to the AED control circuit for receiving communication signals from the AED control circuit and for communicating prompts to the rescuer for use by the rescuer in resuscitating the victim, the prompts being related to the signal communicated to the AED control circuit by a force sensor related to the magnitude of force applied to the force sensor and to the frequency of application of the force to the force sensor.

20. The AED of claim 19 wherein the force sensor is responsive to the relative magnitude of the force applied thereto and communicates a signal related to said force magnitude to the AED control system.

21. The AED of claim 20 wherein the AED control circuit communicates signals relating to the relative magnitude of force applied to the force sensor to the AED prompting means for transmission as a prompt to the rescuer.

22. The AED of claim 21 wherein the AED control system determines the interval between a succession of force applications applied to the force sensor.

23. The AED of claim 22 wherein the AED control circuit communicates signals relating to the interval between a succession of force applications applied to the force sensor to the AED prompting means for transmission as a prompt to the rescuer.

24. An automated electronic defibrillator (AED) for use by an operator in assisting in resuscitating a victim, having a charging circuit for developing a high voltage charge, at least two electrodes for application to the person of a victim, the at least two electrodes being in electrical communication with the charging circuit, a control circuit communicatively coupled to the charging circuit and the electrodes for detecting certain biological parameters of the victim and for controlling the delivery of a voltage charge from the charging circuit through the at least two electrodes to the victim, comprising:

means for prompting a rescuer in the delivery of cardiopulmonary resuscitation (CPR) to the victim, the means for prompting a rescuer including a force sensor applicable to a skin surface of the victim and being responsive to the application of a force to said force sensor, the force sensor having, a first conductive layer;

a second conductive layer being spaced apart from the first conductive layer, the first and second conductive layers being electrically isolated from one another; and electrical communication means for establishing electrical communication between the first and second conductive layers responsive to the application of a force to said electrical communication means.

25. The AED of claim 24 wherein at least a part of the electrical communication means of the force sensor are formed of an extrudable, electrically conductive material, the electrical communication means being extruded by the application of a force to said electrical communication means, at least one extrusion thereof establishing a path of electrical communication between the first and second conductive layers responsive to the application of said force.

26. The AED of claim 25, the force sensor further including a flexible, nonconductive layer being disposed between the first and second conductive layers.

27. The AED of claim 26 wherein the first and second conductive layers of the force sensor are formed of conductive ink printed on opposed sides of the nonconductive layer.

*28. A patient interface for use with an automated electronic defibrillator (AED) comprising:*

*a patient connection interface adapted to be positioned externally on a victim and operably connected to the AED, the patient connection interface including:*

*means for selectively delivering a signal to the AED representative of the victim's cardiac electrical signal;*

*means for selectively delivering a defibrillation shock pulse from the AED to the victim; and*

*means for selectively delivering a signal to the AED indicative of a magnitude of chest compression when the victim is receiving cardiopulmonary resuscitation (CPR).*

*29. The patient connection of claim 28, wherein the means for selectively delivering a signal to the AED comprises at least one sensor having at least one lead wire attached to the sensor.*

*30. The patient connection of claim 29, wherein the sensor is a force sensor, and the signal delivered to the AED is related to a force applied to the sensor.*

*31. A method of interfacing an automated electronic defibrillator (AED) with a victim comprising the steps of:*

*positioning a patient interface externally on the victim, the patient interface having at least two electrodes and at least one sensor;*

*connecting the patient interface to the AED;*

*using the AED to sense a signal representative of the victim's cardiac electrical signal from the at least two electrodes;*

*using the AED to sense a signal from the sensor indicative of a magnitude of chest compression when the victim is receiving cardiopulmonary resuscitation (CPR);*

*determining if the magnitude of chest compressions received by the victim during CPR is effective for resuscitation by using the AED to analyze the signal from the sensor;*

*prompting the rescuer in response to the step of determining if the magnitude of chest compressions received by the victim during CPR is effective; and*

*using the AED to selectively deliver a defibrillation shock pulse from the AED to the victim through the at least two electrodes.*

*32. The patient connection of claim 29, wherein the sensor senses a force applied to the sensor, and wherein the signal from the sensor is proportional to the force applied to the sensor.*

*33. The method of claim 31, wherein the step of determining if the magnitude of chest compressions received by the victim during CPR is effective determines whether the rescuer effectively depressed the sternum between about 4 and 5 cm.*

*34. An automated external defibrillation system for use by a rescuer to resuscitate a victim comprising:*

*a patient connection interface adapted to be positioned externally on a victim, the patient connection interface including:*

*at least two electrodes, each having at least one lead wire attached to the electrode that selectively delivers a signal representative of the victim's cardiac electrical signal (EKG) and that selectively delivers a defibrillation shock pulse to the victim; and*

*at least one sensor having at least one lead wire attached to the sensor that selectively delivers a signal indicative of a magnitude of chest compression when the victim is receiving cardiopulmonary resuscitation (CPR); and*

*an automatic external defibrillator (AED) having:*

*charging circuitry that is in electrical communication with the at least two electrodes via the lead wires and selectively develops a high voltage charge for defibrillation of the victim;*

*EKG cardiac sensing circuitry that is in electrical communication with the at least two electrodes via the lead wires and selectively receives the signal representative of the victim's cardiac electrical signal;*

*CPR sensing circuitry that is in electrical communication with the at least one sensor via the lead wires and selectively receives the signal indicative of the magnitude of chest compressions;*

*voice circuitry that selectively generates audio prompts for the rescuer; and*

*a processor and associated memory and control logic operably connected to the charging circuitry, the EKG sensing circuitry, the CPR sensing circuitry and the voice circuitry that executes programmed instructions to selectively perform the steps comprising:*

*automatically analyzing the victim's cardiac electrical signal;*

*automatically analyzing the signal indicative of the magnitude of chest compression;*

*generating audio prompts to instruct the rescuer on appropriate instructions to perform both CPR and defibrillation based on the steps of analyzing the magnitude of chest compression and the victim's cardiac electrical signal; and*

*controlling delivery of the high voltage charge from the charging circuitry to the victim via the at least two electrodes at a time coordinated with audio prompts that instruct the rescuer.*

*35. The system of claim 34 wherein the processor analyzes the signal indicative of the magnitude of chest compression to determine if the indicated magnitude of chest compression is within a desired range.*

*36. The system of claim 35 wherein the desired range is based on a force and the sensor senses a force applied to the sensor.*

*37. The system of claim 35 wherein the desired range is based on a chest compression and the processor analyzes the signal indicative of the magnitude of chest compression to determine whether the rescuer effectively depressed the sternum between about 4 and 5 cm.*

*38. The system of claim 35 wherein the desired range is based on a rate and the processor analyzes the signal indicative of the magnitude of chest compression to determine a rate of chest compressions.*

*39. An automated external defibrillation system for use by a rescuer to resuscitate a victim comprising:*

*a patient connection interface adapted to be positioned externally on a victim, the patient connection interface including:*

*means for selectively sensing and delivering a signal representative of the victim's cardiac electrical signal (EKG) and for selectively delivering a defibrillation shock pulse to the victim; and*

*means for selectively sensing and delivering a signal indicative of at least one parameter associated with the victim receiving cardiopulmonary resuscitation (CPR); and*

*an automatic external defibrillator (AED) having:*

*means for selectively developing a high voltage charge for defibrillation of the victim in electrical communication with the patient interface;*

*means for selectively generating audio prompts for the rescuer; and*

*means operably connected to the means for selectively developing a high voltage charge and the means for selectively generating audio prompts for the rescuer for selectively controlling operation of the AED, including:*

*means for automatically analyzing the victim's EKG signal;*

*means for automatically analyzing the CPR signal;*

*means for generating audio prompts to instruct the rescuer on appropriate instructions to perform both CPR and defibrillation in response to the means for automatically analyzing the EKG signal and the means for automatically analyzing the CPR signal; and*

*means for selectively delivering the high voltage charge from the means for selectively developing a high voltage charge at a time coordinated with audio prompts generated by the means for generating audio prompts.*

*40. The system of claim 39, wherein the means for selectively sensing and delivering a signal representative of the victim's cardiac electrical signal (EKG) and for selectively delivering a defibrillation shock pulse to the victim comprises a pair of electrodes, each electrode having at least one lead wire attached thereto.*

*41. The system of claim 39, wherein the means for selectively sensing and delivering a signal indicative of at least one parameter associated with the victim receiving CPR comprises a sensor having at least one lead wire attached thereto.*

*42. The system of claim 41, wherein the CPR signal includes a signal indicative of the magnitude of chest compression and the means for automatically analyzing the CPR signal analyzes the signal indicative of the magnitude of chest compression to determine if the magnitude of chest compression is within a desired range.*

*43. The system of claim 42, wherein the desired range is based on a force.*

*44. The system of claim 42, wherein the desired range is based on a rate.*

*45. The system of claim 42 wherein the desired range is based on a chest compression and the means for selectively controlling operation of the AED analyzes the signal indicative of the magnitude of chest compression to determine whether the rescuer effectively depressed the sternum between about 4 and 5 cm.*

*46. A method of prompting a rescuer in the resuscitation of a victim comprising the steps of:*

*positioning a patient connection interface externally on a victim, the patient connection interface including at least two electrodes and at least one sensor;*

*connecting the patient connection interface to an automatic external defibrillator (AED);*

*using the AED and the at least two electrodes to selectively sense and automatically analyze a signal representative of the victim's cardiac electrical signal (EKG);*

*using the AED and the at least one sensor to selectively sense and automatically analyze a signal indicative of a magnitude of chest compression when the victim is receiving cardiopulmonary resuscitation (CPR);*

*automatically causing voice circuitry in the AED to generate audio prompts to instruct the rescuer on appropriate instructions to perform both CPR and defibrillation based on the steps of automatically analyzing the victim's EKG and automatically analyzing the signal indicative of a magnitude of chest compression when the victim is receiving CPR; and*

*automatically causing the AED to selectively deliver a high voltage charge from a charging circuitry to the victim via the at least two electrodes at a time coordinated with audio prompts generated by the voice circuitry.*

* * * * *